US012685645B2

(12) United States Patent
Harris et al.

(10) Patent No.:   US 12,685,645 B2
(45) Date of Patent:      Jul. 21, 2026

(54) INTERBODY IMPLANT AND METHOD

(71) Applicant: FloSpine, LLC, Boca Raton, FL (US)

(72) Inventors: Peter M. Harris, Boca Raton, FL (US); James Q. Spitler, Winter Garden, FL (US); Luis A. Escobar, III, Boca Raton, FL (US); James Szalas, Ft. Lauderdale, FL (US)

(73) Assignee: FloSpine, LLC, Boca Raton, FL (US)

( * ) Notice: Subject to any disclaimer, the term of this patent is extended or adjusted under 35 U.S.C. 154(b) by 397 days.

(21) Appl. No.: 17/962,382

(22) Filed: Oct. 7, 2022

(65) Prior Publication Data

US 2023/0114676 A1      Apr. 13, 2023

Related U.S. Application Data

(60) Provisional application No. 63/253,438, filed on Oct. 7, 2021.

(51) Int. Cl.
A61F 2/44          (2006.01)
A61F 2/30          (2006.01)

(52) U.S. Cl.
CPC ........ A61F 2/4455 (2013.01); A61F 2/30767 (2013.01); A61F 2002/30593 (2013.01)

(58) Field of Classification Search
CPC .............................................. A61F 2/44–447
See application file for complete search history.

(56) References Cited

U.S. PATENT DOCUMENTS

| | | | | |
|---|---|---|---|---|
| 10,772,732 | B1 * | 9/2020 | Miller | .................. A61F 2/30771 |
| 10,779,954 | B1 * | 9/2020 | Northcutt | ................... A61F 2/28 |
| 2005/0177238 | A1 * | 8/2005 | Khandkar | ........... A61L 27/3856 |
| | | | | 623/23.57 |
| 2015/0045903 | A1 * | 2/2015 | Neal | ....................... B22F 5/106 |
| | | | | 219/76.14 |
| 2018/0263785 | A1 * | 9/2018 | Vishnubhotla | .......... A61F 2/447 |
| 2022/0296386 | A1 * | 9/2022 | Fang | ..................... A61F 2/4611 |

FOREIGN PATENT DOCUMENTS

EP            0267624 A2 *  5/1988   ............. A61L 27/12

* cited by examiner

*Primary Examiner* — Nicholas J Plionis
(74) *Attorney, Agent, or Firm* — David Meibos; Maywood IP Law

(57) ABSTRACT

In some implementations, the interbody implant may include an anterior side, a posterior side, a cephalad side, a caudal side, a right side, and a left side. In addition, the interbody implant may include a proximal end and a distal end. The interbody implant may include a mesh having a first set of pores having a first diameter based on a first relationship to a first locus and a second set of pores having a second diameter based on a second relationship to the first locus. Moreover, the interbody implant may include where at least one of the anterior side, posterior side, left side, right side, cephalad side, and caudal side may include the mesh.

9 Claims, 22 Drawing Sheets

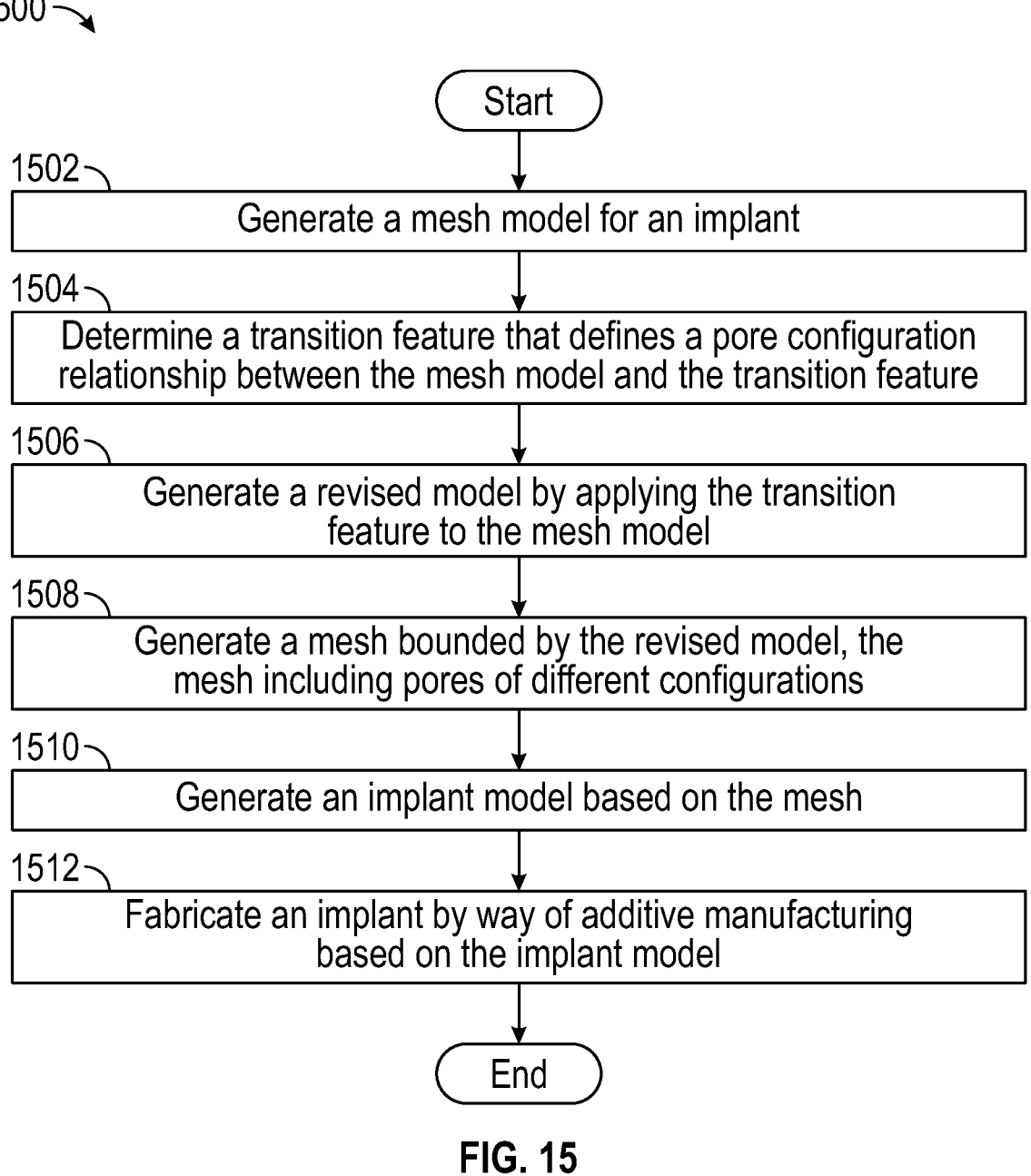

1500

Start

1502
Generate a mesh model for an implant

1504
Determine a transition feature that defines a pore configuration relationship between the mesh model and the transition feature 1506
Generate a revised model by applying the transition feature to the mesh model 1508
Generate a mesh bounded by the revised model, the mesh including pores of different configurations 1510
Generate an implant model based on the mesh 1512
Fabricate an implant by way of additive manufacturing based on the implant model End

INTERBODY IMPLANT AND METHOD

CROSS-REFERENCE TO RELATED APPLICATIONS

This application claims the benefit of U.S. Provisional Application No. 63/253,438, filed Oct. 7, 2021, which is hereby incorporated by reference in its entirety.

TECHNICAL FIELD

The present disclosure relates to surgical devices, systems, instruments, and methods. More specifically, the present disclosure relates to implants used in the spine, such as fusion cages, interbody implants, spinal intervertebral devices, and the like and methods of designing and/or using the same.

BACKGROUND

Various interbody implants exist and come in a variety of shapes, sizes, and configurations. One goal with surgical procedures that deploy implants is to encourage and/or promote osseointegration. Osseointegration is desired to achieve lasting and secure fixation between one or more bones of the patient and the implant. The osseointegration can include bone ingrowth (bone grows into the structure of the implant) and/or bone on growth (bone grows on the surface of the implant).

Interbody implants need to be strong and capable of supporting loads in the spine and a variety of forces after implantation. Thus, interbody implants can be made from metals such as titanium. Metal interbody implants can provide the desired strength but can block effective imaging of areas within the implant, such as a graft opening. The structural components of the interbody implant can block x-ray or fluoroscopic imaging of open areas within the interbody implant. What is needed is an interbody implant that provides sufficient strength, has a suitable amount of porosity to support full osseointegration, and enables visual inspection of areas internal to the interbody implant using conventional imaging techniques. The present disclosure provides embodiments of interbody implants that address this need.

SUMMARY

The various apparatus, devices, systems, and/or methods of the present disclosure have been developed in response to the present state of the art, and in particular, in response to the problems and needs in the art that have not yet been fully solved by currently available technology.

One general aspect of the present disclosure can include an interbody implant that may include an anterior side, a posterior side, a cephalad side, a caudal side, a right side, and a left side. The interbody implant may also include a proximal end and a distal end. The interbody implant may furthermore include a mesh having a first set of pores having a first diameter based on a first relationship to a first locus and a second set of pores having a second diameter based on a second relationship to the first locus. The interbody implant may in addition include where at least one of the anterior side, posterior side, left side, right side, cephalad side, and caudal side may include the mesh.

The described implementations may also include one or more of the following features. An interbody implant where the mesh may include a mesh surface formed within a gyroid triply periodic minimal surface (TPMS) field, the mesh surface volumized and where the mesh may include pores that vary in diameter based on a position of a pore in relation to a first locus between a maximum pore size and a minimum pore size. The interbody implant may include a third set of pores having diameters that vary between the first diameter and the second diameter. The interbody implant may include a mesh where the mesh forms at least one of the anterior side, the posterior side, the left side, and the right side and the first locus intersects the mesh. An interbody implant where the first relationship and the second relationship each may include a distance of a set of pores from the first locus and where the mesh forms the posterior side and one of the left side and the right side and the first locus intersects the posterior side and the one of the left side and the right side. An interbody implant where the first locus intersects the posterior side and the left side at a posterior side midpoint and at a left side midpoint. An interbody implant where: the first locus may include an X shape; and where the first locus intersects a posterior side midpoint, an anterior side midpoint, a left side midpoint, and a right side midpoint. An interbody implant where the mesh may include a second locus and the pores of the mesh vary in diameter based on a position of a pore in relation to the first locus and the second locus. An interbody implant where: the posterior side is connected to the left side at a first corner, the left side is connected to the anterior side at a second corner, the anterior side is connected to the right side at a third corner, and the right side is connected to the posterior side at a fourth corner such that posterior side, left side, anterior side, and right side form an implant profile in a caudal view; interbody implant may include four pillars, each pillar positioned in one of the first corner, the second corner, the third corner, and the fourth corner of the interbody implant; the pillars cooperate to define a cross-section that forms a pillars profile smaller than the implant profile; a graft opening that extends through the interbody implant from the cephalad side to the caudal side; and one or more corners between two of the anterior side, left side, right side, and posterior side.

One general aspect of the present disclosure can include a cervical interbody implant. The cervical interbody implant may include a cephalad side having an external top edge and an internal top edge. The cervical interbody implant may also include a caudal side having an external bottom edge and an internal bottom edge. The cervical interbody implant may furthermore include a sidewall that connects to the cephalad side and caudal side and circumscribes a graft opening that extends through the cephalad side and the caudal side, the sidewall having: an engagement feature; and a mesh formed within a gyroid triply periodic minimal surface (TPMS) field and volumized, the mesh having pores that vary in diameter based on a position of a pore within the sidewall between a maximum pore size and a minimum pore size. The cervical interbody implant may in addition include an external cephalad frame member that traverses at least part of the external top edge. The cervical interbody implant may moreover include an internal cephalad frame member that traverses at least part of the internal top edge. Implant may also include an external caudal frame member that traverses at least part of the external bottom edge. The cervical interbody implant may furthermore include an internal caudal frame member that traverses at least part of the internal bottom edge. Implant may in addition include where the cervical interbody implant has a proximal end and a distal end.

Implementations may include one or more of the following features. A cervical interbody implant where: the graft opening may include a cross-section shape having four sides each connected to two curved corners, the cervical interbody implant may include a four pillars, each positioned near a curved corner of the graft opening; and where the pores of the mesh vary in diameter between each curved corner and a midpoint between two adjacent curved corners. A cervical interbody implant where the pores of the mesh having the maximum pore size form a radiolucent window into the graft opening. A cervical interbody implant where the cervical interbody implant may include: a compressive strength of between about 28 Kilo-Newtons and about 36 Kilo-Newtons measured with a load pressing the cephalad side and the caudal side towards each other; a density of between about 2 grams per centimeter cubed to about 2.5 grams per centimeter cubed; and a stiffness of between about 31 Kilo-Newtons per millimeter and about 36 Kilo-Newtons per millimeter. A cervical interbody implant where a plurality of the pores of the mesh extend from the graft opening to an external surface of the sidewall. A cervical interbody implant where a plurality of the pores vary in diameter based on a position of a pore within the sidewall and a transition feature.

Some implementations herein relate to a method. For example, a method may include generating a mesh model for an implant. A method may also include determining a transition feature that factors into a pore configuration relationship between the mesh model and the transition feature. A method may furthermore include generating a revised model by applying the transition feature to the mesh model. A method may in addition include generating a mesh bounded by the revised model, the mesh including pores of different configurations. A method may moreover include generating an implant model based on the mesh. A method may also include fabricating an implant by way of additive manufacturing based on the implant model.

The described implementations may also include one or more of the following features. A method where the transition feature may include a transition model and where the transition feature may include a first pore size, and a second pore size, and where the pore configuration relationship may include a modification of a mesh pore size for the mesh based on a distance between a mesh position within the mesh model and an intersection of the mesh model with the transition model. A method where the modification of the mesh pore size may include decreasing pore diameter size for pores of the mesh from the first pore size down to the second pore size based on an increasing distance between a mesh position within the mesh model and an intersection of the mesh model with the transition model. A method where the transition model may include a three dimensional X shape having a common origin with the mesh model and positioned such that one or more legs of the three dimensional X shape intersect the mesh model at a midpoint of four sides of the mesh model. A method where generating the mesh bounded by the revised model may include: generating a triply periodic minimal surface (TPMS) field; mapping the revised model into the TPMS field to generate a mesh surface bounded by the revised model, the mesh surface including pores; and volumizing the mesh surface to generate the mesh bounded by the revised model. Implementations of the described techniques may include hardware, a method or process, or a computer tangible medium.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 15 illustrates one example of a method for making an implant that has variable size pores.

DETAILED DESCRIPTION

Figure 1:
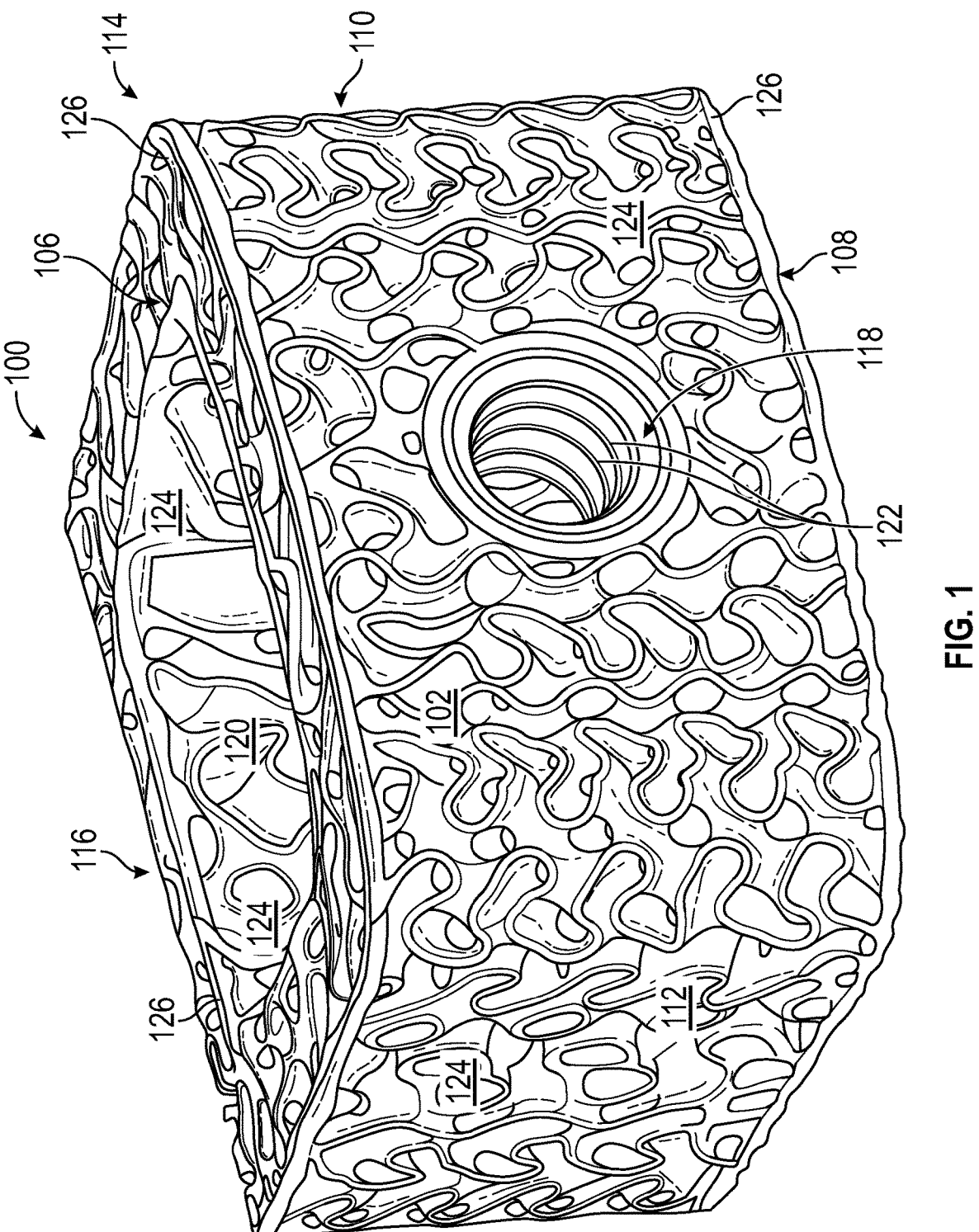
FIG. 1 is a perspective view of an interbody implant, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. For example, components and/or elements of one embodiment can be combined in a variety of ways with other components and/or elements of another embodiment to form a new embodiment. Thus, the following more detailed description of the embodiments of the apparatus, system, and method is not intended to limit the scope of the invention, as claimed, but is merely representative of exemplary embodiments of the technology.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

The present disclosure discloses surgical devices, systems, and/or methods for fixation of tissue within a body of a patient. Known fixators and/or fixation devices, methods, or steps are limited. Fixation devices may be aperture fixation (e.g., interference screws) or suspensory fixation (e.g., EZLoc, WasherLoc, Toggleloc plus EZloc, and the like; cortical: Endo buttons, staples, screw posts; cancellous: transfixion pins, Bio-TransFix, Aperfix, and the like). A simple, easy fixation device that facilitates setting a tension in soft tissue is needed.

The present disclosure discloses a fixation device and/or method for fixation of tissue that is quick and easy to deploy, low profile, readily revisable, requires no special knots or supporting accessories or equipment, and provides a strong fixation that is secure and provides the desired level of fixation in view of tensions experienced by tissue in a joint such as a knee.

Referring to FIGS. 1-6, an interbody implant 100 has an anterior side 102, a posterior side 104, a cephalad side 106, a caudal side 108, a right side 110, and an opposite left side 112. The interbody implant may have a variety of shapes and sizes. Those of skill in the art will recognize that the interbody implant 100 is design specific to a cervical fusion or repair procedure. Of course, the embodiments of the present disclosure can be used for thoracic and lumbar implants as well.

In one embodiment, the interbody implant 100 is rectangular having a right side 110 and left side 112 that are longer than a cephalad side 106 and a caudal side 108. In one embodiment, the right side 110 and left side 112 may be of similar length and the cephalad side 106 and caudal side 108 may be of similar length. The interbody implant 100 may also include a proximal end 114 and a distal end 116.

The interbody implant 100 may also include an engagement feature 118 and a graft opening 120. The engagement feature 118 may include internal threads 122. The engagement feature 118 may connect to an inserter (not shown) by way of a threaded engagement between the internal threads 122 and a corresponding engagement feature of the inserter. A surgeon may use the inserter to deploy the interbody implant 100 and after desired deployment and positioning disengage the inserter and the interbody implant 100 to deploy the interbody implant 100. In the illustrated embodiment, the surgeon deploys the interbody implant 100 using an anterior approach to the spine.

The graft opening 120 may serve to hold graft tissue and/or a graft composition such as a bone graft. In certain embodiments, the graft opening 120 is sized to be large enough to hold a sufficient amount of bone graft to achieve a desired outcome for a surgical procedure that uses the interbody implant 100.

In certain embodiments, the interbody implant 100 may include a mesh 124 and a frame 126 that may connect to, and/or define, one or more edges of the interbody implant 100. In the illustrated embodiment, the cephalad side 106 of the interbody implant 100 may include an external top edge 302, an internal top edge 304, and the caudal side 108 of the interbody implant 100 may include an external bottom edge 306, and an internal bottom edge 308 (See FIG. 3).

In certain embodiments, the frame 126 is made up of one or more frame members. The frame members may be solid structures. For example in the illustrated embodiment, the frame 126 includes an external cephalad frame member 310, an internal cephalad frame member 312, an external caudal frame member 314, and an internal caudal frame member 316 (See FIG. 3). Together the frame members can form a frame 126 that can provide added stability to the interbody implant 100.

The external cephalad frame member 310, internal cephalad frame member 312, external caudal frame member 314, and/or internal caudal frame member 316 may traverse one or more edges of the interbody implant 100. In one embodiment, the external cephalad frame member 310 may traverse at least part of the external top edge 302. Note that in the illustrated embodiment, the external cephalad frame member 310 may not traverse an external top edge 302 of the posterior side 104. Similarly, referring to FIG. 3, the external caudal frame member 314 may traverse at least part of the external bottom edge 306. Note that in the illustrated embodiment, the external caudal frame member 314 may not traverse an external bottom edge 306 of the posterior side 104. In the illustrated embodiment, the internal cephalad frame member 312 circumscribes the internal top edge 304 and the internal caudal frame member 316 may circumscribe the internal bottom edge 308. In the illustrated embodiment, the internal cephalad frame member 312 and/or internal caudal frame member 316 may also circumscribe the graft opening 120.

The frame members may provide structural support for the interbody implant 100. Alternatively, or in addition, the frame members may close off loose or cantilevered portions of a mesh 124 that may form on one or more sides of the interbody implant 100.

In one embodiment, the mesh 124 may form one or more of the anterior side 102, posterior side 104, cephalad side 106, caudal side 108, right side 110, and left side 112. In one or more other embodiments, one or more sides of the interbody implant that do not include a mesh may be solid or may include one or more windows. Those of skill in the art will appreciate that one side of the interbody implant 100 may be formed by the mesh 124 or two sides of the interbody implant 100 may be formed by the mesh 124, or three sides of the interbody implant 100 may be formed by the mesh 124 or all sides of an interbody implant may be formed by the mesh 124.

In the illustrated embodiment of FIGS. 1-6, the mesh 124 forms a single unitary structure that forms each of the anterior side 102, posterior side 104, cephalad side 106, caudal side 108, right side 110, and left side 112. In such an embodiment, the mesh 124 may be referred to as a sidewall. In such an embodiment, sidewall may connect to the cephalad side 106 and caudal side 108 and circumscribe the graft opening 120 may include an engagement feature 118 and the mesh 124.

Advantageously, the mesh 124 includes a plurality of pores 128. In certain embodiments, the pores 128 are through pores which permit passage of fluids, gases, and other particulates through the mesh 124. In other embodiments, the mesh 124 may include one or more pores that are dead end pores that do not permit passage through the mesh 124.

In certain embodiments, the pores 128 vary in diameter through a certain area of the mesh 124. In particular, in one embodiment, the pores 128 vary in diameter about, or in relation to, a first locus 130. In certain embodiments, one or more sides (e.g., 102, 104, 110, and 112) of the interbody implant 100 may include a first locus 130. The first locus 130 may define an area within a side that determines a size for one or more pores formed in the mesh 124. The first locus 130 may be defined using various techniques, formulae, algorithms, representations, and/or models. For example, a geometric point, line, plane, 2D shape, or 3D shape in a three-dimensional coordinate system may define a locus, such as a first locus 130. Alternatively, or in addition, a mathematical formula and/or an algorithm may define the locus for a mesh 124. A locus serves as a reference for another characteristic, attribute, or feature. In the illustrated embodiment, the other characteristic, attribute, or feature can be pore diameter size.

In certain embodiments, the first locus 130 intersects the mesh 124. Alternatively, or in addition, the first locus 130 may be at a position that does not intersect the mesh 124. For example, the first locus 130 can be at a center of the graft opening 120 or at any position outside the graft opening 120.

In certain embodiments, the mesh 124 may form less than each side of the interbody implant 100. Advantageously, the relationship of pore sizes for pores in the mesh 124 to a first locus 130 can form a radiolucent window 134 in a side that includes the mesh 124. Consequently, in one embodiment two of four sides of the interbody implant 100 may include the mesh 124 with pores having pore sizes that vary in relation to a first locus 130. For example, the posterior side 104 and one or the other of the right side 110 and left side 112 may be formed by mesh 124. Furthermore, the posterior side 104 and one or the other of the right side 110 and left side 112 may each include and intersect with a first locus 130. In this manner, the posterior side 104 and one of the right side 110 and the left side 112 will each include a radiolucent window 134. These radiolucent windows 134 can facilitate imaging evaluations of bone osseointegration within the graft opening 120.

The radiolucent window 134 can be of any shape. In certain embodiments, the radiolucent window 134 is a rectangular three dimensional structure. In one embodiment, the radiolucent window 134 is formed by pores 128 of the mesh 124 having a maximum pore size. Advantageously, the radiolucent window 134 provides a radiolucent view of the inside of the graft opening 120, particularly when viewed perpendicular to one of the anterior side 102, posterior side 104, right side 110, and/or left side 112. In this manner, the strength of the mesh 124 provides the strength needed for the interbody implant 100 and the radiolucent window 134 enables a user to view progress of osseointegration within the graft opening 120.

In the exemplary embodiment of FIGS. 1-6, the first locus 130 may be an area or range along a length of each side of an interbody implant 100 or a model or other representation of the interbody implant 100 that extends from a top edge (e.g., external top edge 302) of a side to a bottom edge (e.g., external bottom edge 306) of the side. In certain embodiments, pores formed within the first locus 130 may each have a predetermined diameter, such as 500 micrometers, or less. As pores are calculated, generated, designed, engineered, rendered, or formed in other mesh positions, the diameter of the pore may be based on a distance of the mesh position from the first locus 130.

For example, in one embodiment, each pore formed a further distance away from the first locus 130 may have a smaller diameter than a previous pore having a shorter distance away from the first locus 130. In one embodiment, the diameter may continue to decrease until a minimum diameter is reached. In one embodiment, after the minimum diameter is reached pores may have the minimum diameter even though they are further from the first locus 130 than neighboring pores.

Alternatively, or in addition, in another embodiment, each pore formed a further distance away from the first locus 130 may have a greater diameter than a previous pore positioned closer to the first locus 130. In one embodiment, the diameter may continue to increase until a maximum diameter is reached. In this manner, the pore size or pore diameter size may change and be different for pores that are progressively further and further away from the first locus 130.

In embodiments of an interbody implant 100 having a sidewall that includes a mesh 124 that forms the sidewall, the pores 128 of the mesh 124 may vary in diameter based on a position of a pore within the sidewall between a maximum pore size and a minimum pore size. In one example, the maximum pore size may be between about 500 and 600 micrometers and the minimum pore size may be between about 200 and 300 micrometers. FIGS. 1-6 illustrate an embodiment of the interbody implant 100 in which the pores vary from a minimum pore size near corners of the interbody implant 100 to a maximum pore size near a midpoint 132 (See FIG. 2) along a side of the interbody implant 100. As described in more detail herein, the mesh 124 may be formed within a gyroid triply periodic minimal surface (TPMS) field that is then volumized to form the mesh 124.

The aspect of a pore size that changes in relation to where the pore exists in a mesh relative to a distance between the pore (its mesh position) and one or more references, such as a first locus 130, is one example of a pore configuration relationship. A pore configuration relationship is a relationship, or association, between an attribute, feature, or configuration aspect of a pore relative to one or more references and a determinable attribute. In the example described above, in the pore configuration relationship the attribute is pore diameter (aka pore size), the reference is the first locus 130, and the determinable attribute is a distance between the pore and the reference.

Those of skill in the art will appreciate other configuration aspects, features, or attributes that may be varied using a pore configuration relationship. For example, in another embodiment, a shape of each pore (e.g., cross sectional shape) may vary based on a distance of the pore from a reference such as a first locus 130. In such an embodiment, the shape may vary between circle, square, diamond, rectangle, star, and the like.

Figure 2:
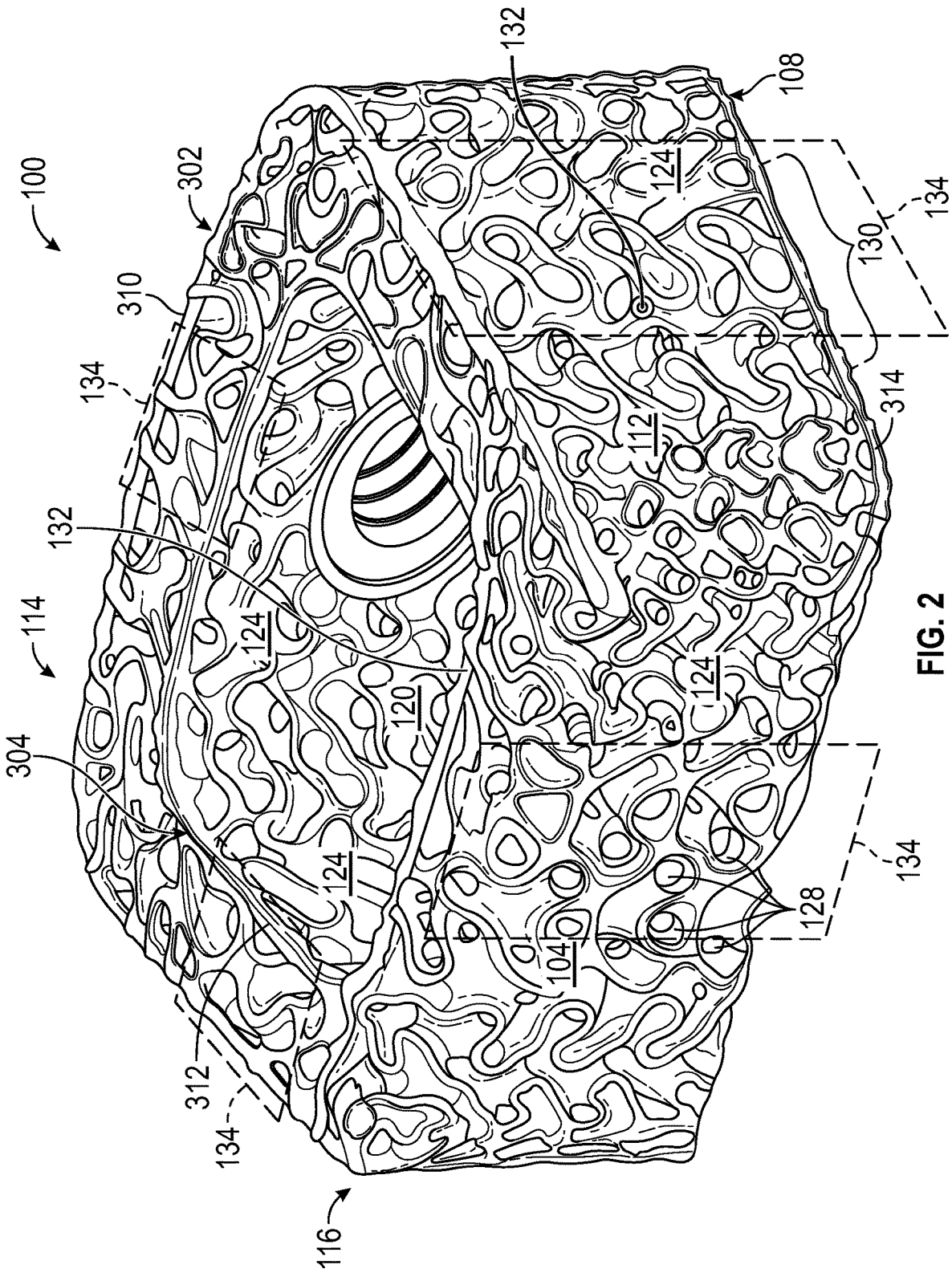
FIG. 2 is another perspective view of the interbody implant of FIG. 1 from a posterior direction, according to one embodiment.

In another example, in the illustrated embodiment, the first locus 130 may be an area that includes a midpoint along one side of the interbody implant 100. The midpoint may be the midpoint as measured between the proximal end 114 and the distal end 116, for example, for a right side 110 or a left side 112 and between a top and a bottom of the right side 110 or left side 112. Similarly, the midpoint may be the midpoint as measured between the proximal end 114 and the distal end 116, for example, for a cephalad side 106 or caudal side 108 and between a right side 110 and a left side 112 of the cephalad side 106 and caudal side 108. Similarly, the midpoint may be the midpoint as measured between the cephalad side 106 and the caudal side 108, for example, for an anterior side 102 or a posterior side 104 and between a right side 110 and a left side 112 of the cephalad side 106 and caudal side 108. As an example, one midpoint 132 is indicated in FIG. 2 on the left side 112.

Figures 3, 4:
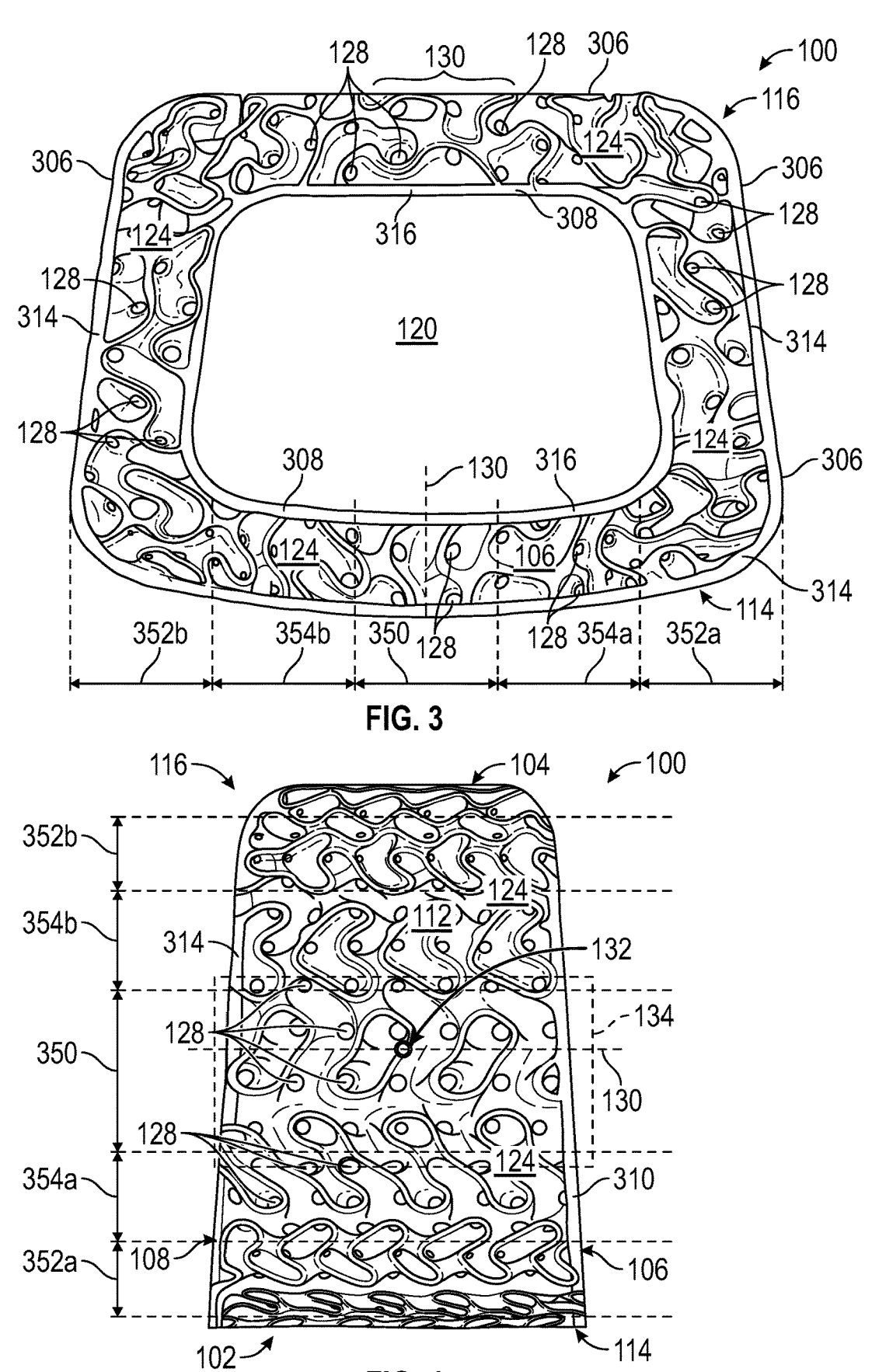
FIG. 3 is a bottom view of the interbody implant of FIG. 1, according to one embodiment.
FIG. 4 is a left view of the interbody implant of FIG. 1, according to one embodiment.

FIG. 3 illustrates a bottom view with like components indicated using the same numbers as the embodiment illustrated in FIGS. 1-6. The top of the interbody implant 100 may be substantially similar to the bottom view.

FIG. 4 illustrates a side view with like components indicated using the same numbers as the embodiment illustrated in FIGS. 1-6. The left side 112 is illustrated. The right side 110 of the interbody implant 100 may be substantially similar to the left side 112. FIG. 4 illustrates that in certain embodiments, The cephalad side 106 and/or the caudal side 108 may each have a slope of the side between the proximal end 114 and the distal end 116. Alternatively, or in addition, in other embodiments, the cephalad side 106 may be parallel to the caudal side 108. In certain embodiments, the slope may relate to the Lordotic angle and may be 7 degrees, 9 degrees or 10 degrees. In FIG. 4 the slope is 7 degrees.

Referring now to FIGS. 3 and 4, in one embodiment, pores 128 of the mesh 124 can be configured into sets of pores that each have a relationship with a first locus and/or a second locus. FIGS. 3 and 4 illustrate that the mesh 124 can include a first set of pores 350 having a first diameter based on a first relationship with the first locus 130. In the illustrated embodiment, the first locus 130 may be a line, or plane, at a midpoint between two opposite ends of a side (e.g., anterior side 102). In addition, the mesh 124 can include a second set of pores 352 having a second diameter based on a second relationship with the first locus 130.

Referring to FIG. 3 the first diameter may be a maximum diameter for pores of the interbody implant 100, such as 500 micrometers. Such a maximum diameter may provide a desirable tradeoff between structural integrity, strength, promoting osseointegration, and permitting imaging of areas within the graft opening 120. The second diameter may be a minimum diameter for pores of the interbody implant 100, such as 200 micrometers. Such a minimum diameter may provide increased structural integrity and minimal imaging transparency since the second set of pores 352 may be more in line with a side of the interbody implant 100 rather than in line with the graft opening 120.

In one embodiment, the maximum diameter may be 600 micrometers. In another embodiment, the maximum diameter may be 400 micrometers. In one embodiment, the minimum diameter may be 100 micrometers. In another embodiment, the minimum diameter may be 300 micrometers.

In the illustrated embodiment, the first relationship and the second relationship may be the same and may include a distance of a set of pores from the first locus 130. Alternatively, the first relationship and the second relationship may be the same and may include a distance of a pore in the set of pores from the first locus 130. For example, the first relationship and the second relationship may be that a pore diameter is a maximum diameter (e.g., the first diameter) when the pore mesh position is within 3 mm of the first locus 130 and the pore diameter may decrease to a minimum diameter (e.g., the second diameter) when the pore mesh position is greater than 5 mm from the first locus 130. In addition, the mesh 124 may include a third set of pores 354 having a plurality of diameters that vary between the first diameter and the second diameter. In the illustrated embodiment, pore sizes of pores in the third set of pores 354 may get progressively smaller as the mesh position of the pore is further away from the first locus 130.

In one embodiment, the relationships between pore sizes and the first locus 130 may be a linear relation based on distance. Consequently, pores in second set of pores 352a may have a similar size and variability to the second set of pores 352a on an opposite side of the first locus 130. The third set of pores 354a and third set of pores 354b may be similarly related to each other. Those of skill in the art will appreciate that the relationships of pore sizes to the first locus 130 may be different and may be linear, exponential, quadratic, or the like.

In another embodiment, the first relationship and the second relationship may be different such that the variation among pores 128 in the mesh 124 for the first set of pores 350 may be different from the variation affecting pores 128 in the second set of pores 352. FIG. 4 illustrates a first set of pores 350, second set of pores 352a,b, and third set of pores 354a,b for one of the sides (e.g., right side 110 and/or left side 112). Note the sizes of the sets and/or numbers of pores 128 in the sets may be different where the length of the side is different from another side of the interbody implant 100.

Figures 5, 6:
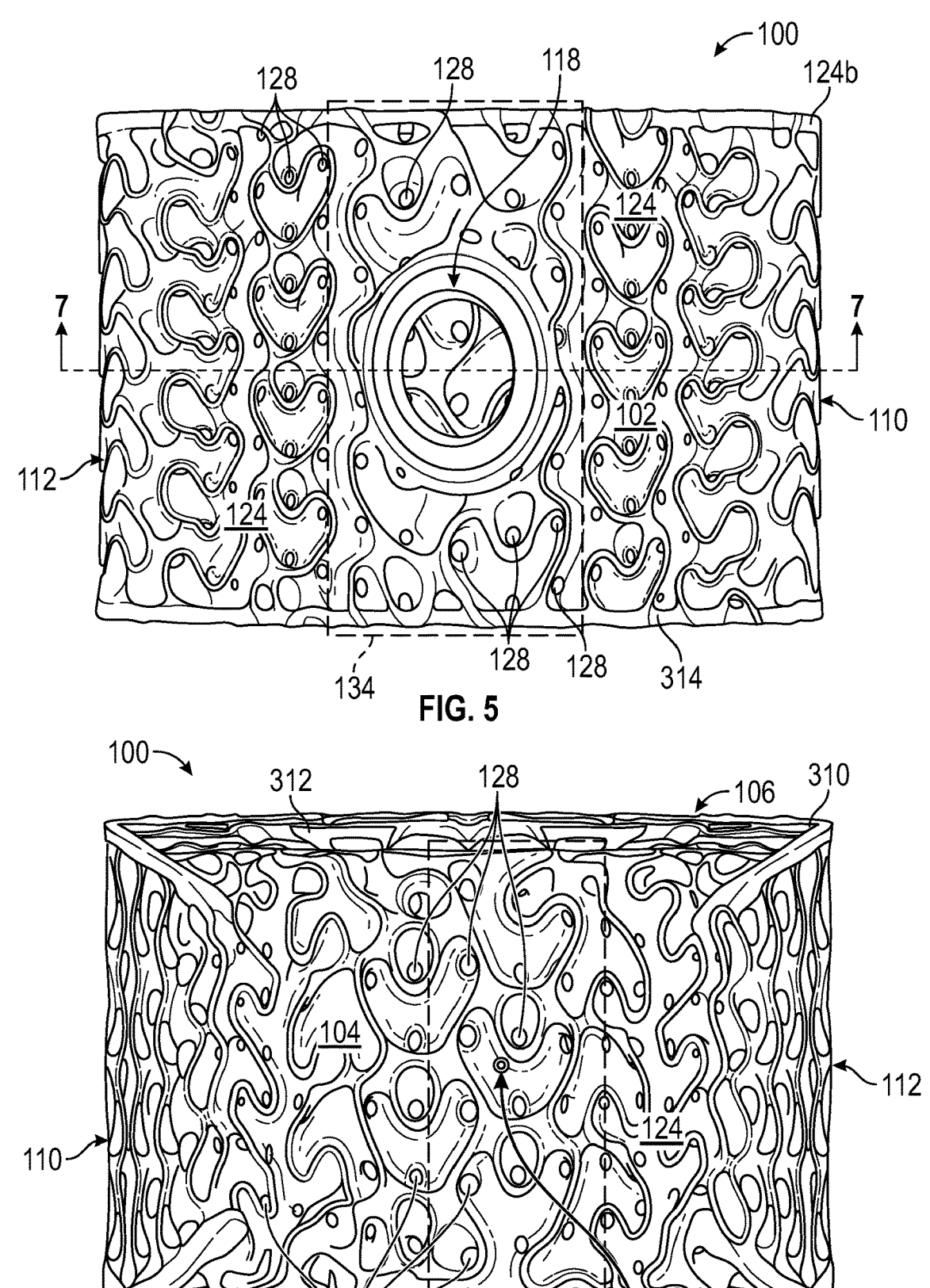
FIG. 5 is a front view of the interbody implant of FIG. 1, according to one embodiment.
FIG. 6 is a back view of the interbody implant of FIG. 1, according to one embodiment.

FIG. 5 illustrates a front or anterior view with like components indicated using the same numbers as the embodiment illustrated in FIGS. 1-6. FIG. 5 includes a cross-section line 7-7 which indicates where the cross-section is taken for FIG. 7.

FIG. 6 illustrates a rear or posterior view with like components indicated using the same numbers as the embodiment illustrated in FIGS. 1-6. FIG. 6 illustrates that in this embodiment, the right side 110 and left side 112 can taper as these sides approach the posterior side 104 (the distal end 116). Consequently, the posterior side 104 may be smaller (in height and/or width) than the anterior side 102.

Figure 7A:
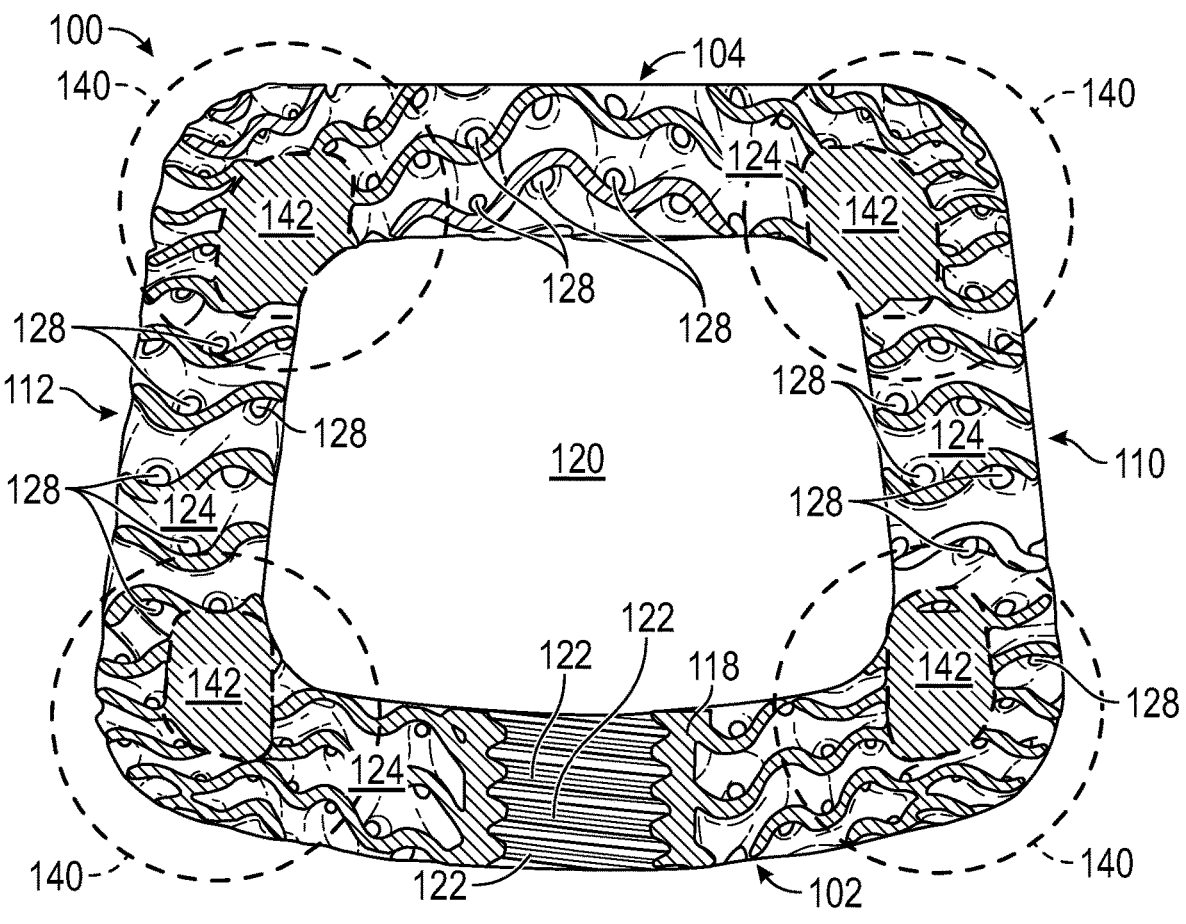
FIG. 7A is a section view of the interbody implant of FIG. 5 taken through line 7-7, according to one embodiment.

FIG. 7A illustrates section view of the interbody implant 100 of FIG. 5 taken through line 7-7, according to one embodiment with like components indicated using the same numbers as the embodiment illustrated in FIGS. 1-6. FIG. 7A illustrates that in one embodiment, the interbody implant 100 can include one or more corners 140. In the illustrated embodiment, the corner 140 may be curved corners. The interbody implant 100 may also include a pillar 142 in one or more of the corners 140. The pillars 142 may be placed at any position within a corner 140. In the illustrated embodiment, the pillars 142 are positioned near the inner part of the corners 140 can may contact or connect with the graft opening 120. In one embodiment, the pillars 142 may extend from the cephalad side 106 to the caudal side 108. Alternatively, or in addition, the pillars 142 may extend from near the cephalad side 106 to near the caudal side 108. The pillars 142 may serve to provide structural support for the interbody implant 100 as the interbody implant 100 supports a load when deployed between two vertebrae. The pillars 142 may have any cross-sectional shape including, but not limited to a rectangle, a square, or other polygon, as well as a circle, an ellipse, an ovoid, a non-geometric shape, or other circular or semi-circular shape. The shape, size, configuration, number, and/or position of the pillars 142 can be predetermined to provide a desired level of rigidity, support, and durability for the interbody implant 100.

The engagement feature 118 and pillars 142 are two examples of implant structure that may be included in an interbody implant 100. In certain embodiments, these implant structures may be the only structures of an interbody implant 100 that are not made from the mesh 124. In certain embodiments, the interbody implant 100 may be fabricated using additive manufacturing.

Figure 7B:
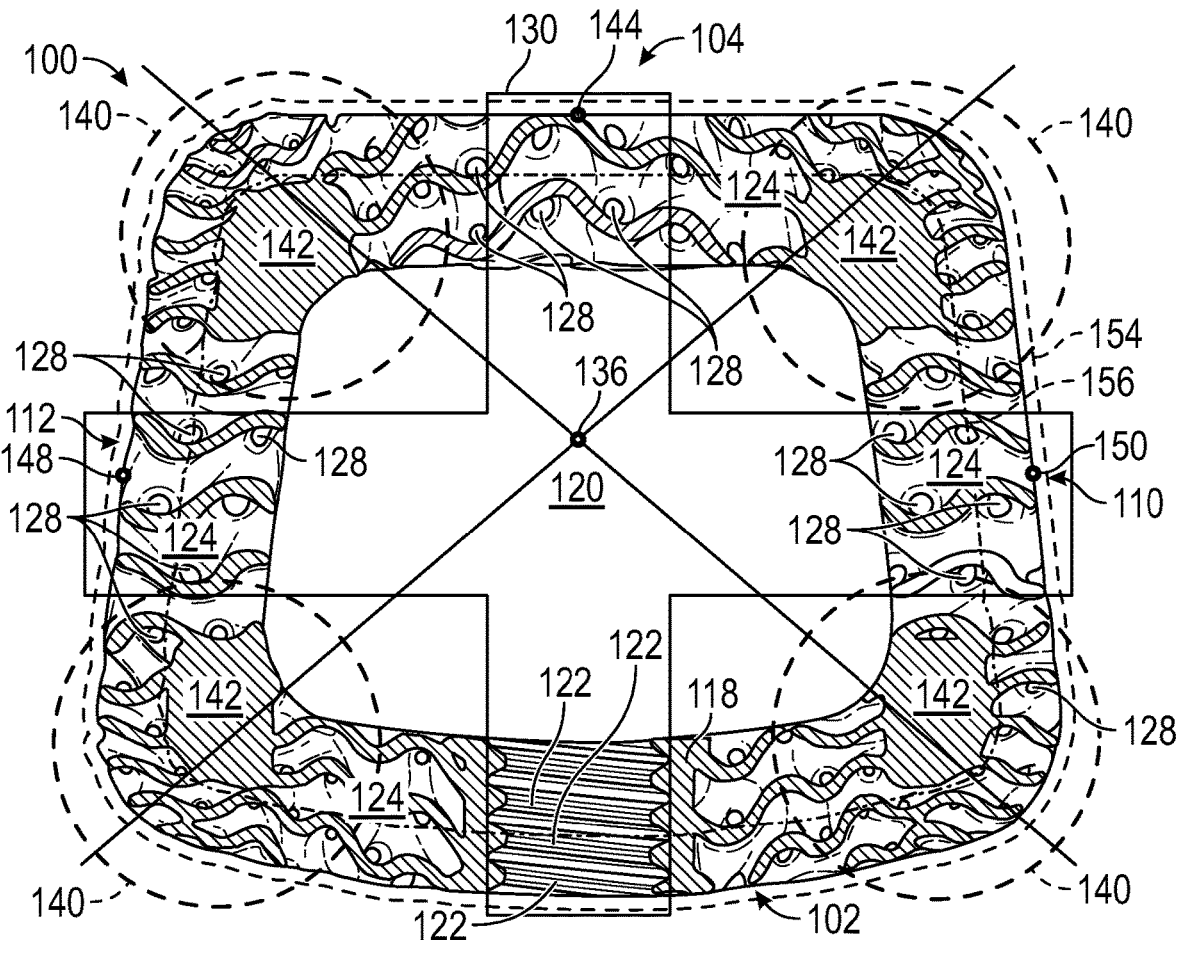
FIG. 7B is a section view of the interbody implant of FIG. 5 taken through line 7-7, according to one embodiment.
Figure 8:
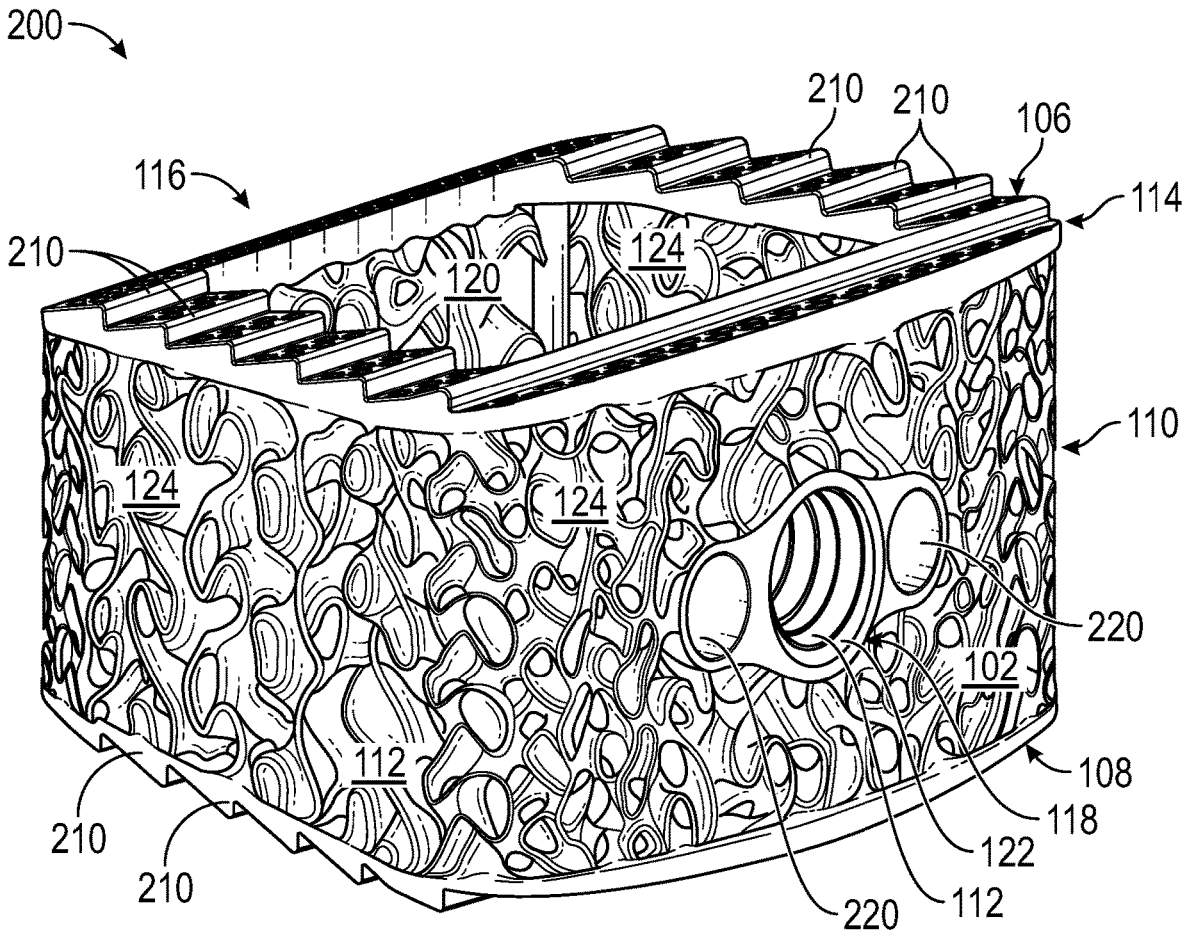
FIG. 8 is a perspective view of an interbody implant, according to one embodiment.

Referring to FIG. 7B, the interbody implant 100 may include a first locus 130 shaped like an X, such as a three dimensional X, in which legs of the X intersect with the anterior side 102, posterior side 104, right side 110, left side 112, cephalad side 106 and, caudal side 108. One leg of the first locus 130 may intersect the posterior side 104 at the posterior side midpoint 144. Another leg of the first locus 130 may intersect the anterior side 102 at the anterior side midpoint 146. Another leg of the first locus 130 may intersect the left side 112 at the left side midpoint 148. Another leg of the first locus 130 may intersect the right side 110 at the right side midpoint 150.

The pores 128 of the mesh 124 are largest closest to the first locus 130. Alternatively, or in addition, the interbody implant 100 may include a second locus 136. The diameter of pores 128 of the mesh 124 may vary in diameter based on a position of a pore 128 in relation to the first locus 130 and the second locus 136.

In the illustrated embodiment, the second locus 136 may also be in the shape of an X but legs of the X shape may be narrow. The legs of the second locus 136 may intersect with the corners 140 of the interbody implant 100. Pores 128 near the second locus 136 may have a minimum diameter. The legs of the second locus 136 may also intersect the pillars 142.

Of course, the first locus 130 and/or second locus 136 may have a variety of shapes. For example, the first locus 130 may be shaped to intersect just two sides of the interbody implant 100. In such an example, the first locus 130 may be shaped like a sideways "L" or a right angle such that the first locus 130 intersects the posterior side 104 and one of the sides adjacent to the posterior side 104, such as the left side 112 or the right side 110. In one embodiment, the first locus 130 intersects the posterior side 104 at a posterior side midpoint 144 and the left side 112 at a left side midpoint 148. The second locus 136 may have the same shape and position as illustrated in FIG. 7B.

In another embodiment, the first locus 130 may intersect the posterior side 104, the right side 110, and the left side 112. For example the first locus 130 may be shaped like a letter "T" with the vertical part of the "T" intersecting with the posterior side 104 and one arm of the "T" intersecting the right side 110 and the other arm of the "T" intersecting the left side 112.

FIG. 7B illustrates that the posterior side 104 is connected to the left side 112 at a first corner 140. The left side 112 is connected to the anterior side 102 at a second corner 140. The anterior side 102 is connected to the right side 110 at a third corner 140. The right side 110 is connected to the posterior side 104 at a fourth corner 140.

The interbody implant 100 includes a graft opening 120 having a cross-sectional shape 152 that has four sides, each side is connected to two curved corners 140. The pillar 142 are positioned near the corners 140. The pores 128 of the mesh 124 may vary between each curved corner and a midpoint between two adjacent corners. The graft opening 120 extends from the cephalad side 106 to the caudal side 108.

Together the posterior side 104, left side 112, anterior side 102, right side 110 form an implant profile 154 in a caudal view (viewed from the caudal side 108, in certain embodiments, the caudal view and cephalad view of the cross-section in FIG. 7B may be the same). In the illustrated embodiment, the corners 140 are round or curved corners.

FIG. 7B illustrates that the interbody implant 100 includes four pillars 142 each positioned in or near one of the corners 140. The pillar 142 cooperate to define a cross-section that forms a pillars profile 156 that is smaller than the implant profile 154. The pillars profile 156 may be formed by offsetting the pillars 142 in relation to the implant profile 154. The offset pillars 142 can provide more surface area for osseointegration at an external surface of the interbody implant 100.

Advantageously, the smaller implant profile 154 provides more structural space for the mesh 124. In particular, an outside area between an external surface of a corner 140 and the pillar 142 is formed by the mesh 124. The outside area can further promote osseointegration. In the illustrated embodiment, one side of pillars 142 form part of an internal surface of the graft opening 120. Of course, the pillar 142 can be offset further away from the graft opening 120 such that an internal area is formed between the pillar 142 and the graft opening 120 that can also be formed from mesh 124.

FIG. 7B illustrates an embodiment of an interbody implant 100 in which the pillars 142 have a cross-sectional shape other than a conventional geometric shape (e.g., circle, square, rectangle, oval, triangle, and the like). Instead, the cross-sectional shape of the pillar 142 may include sides that are straight and sides that are curved. In one embodiment, one or more curved sides of the cross-sectional shape of the pillar 142 can have the same or a similar curve shape as an external corner of the implant profile 154.

While embodiments of the interbody implant 100 can include pillars 142 with cross-sectional shape of conventional geometric shapes, other embodiments may not include such a shape in order to recognize other advantages. In the illustrated embodiment, the cross-sectional shape of the pillar 142 may have opposite side curved sections joined by straight sections. Such a cross-sectional shape of the pillar

142 may enable more use of the mesh 124 and/or more effective integration with the mesh 124. In other words, the cross-sectional shape of the pillar 142 may be configured to enhance the number of pores 128 in the interbody implant 100. A higher number of pore 128 may enhance the osseointegration features of the interbody implant 100.

In one embodiment, the interbody implant 100 may comprise an interbody implant 100 design specifically for use between the smaller vertebrae of the cervical section of the spine. In such an embodiment, the interbody implant 100 may be referred to as a cervical interbody implant. Advantageously, the mesh 124, frame 126, pores 128, pillars 142, and overall design of the interbody implant 100 and the material of the interbody implant 100 being a metal such as titanium can provide desirable characteristics for a cervical interbody implant.

For example in one embodiment, the interbody implant 100 may have a compressive strength of between about 28 Kilo-Newtons and about 36 Kilo-Newtons measured with a load pressing the cephalad side 106 and the caudal side 108 towards each other. In another embodiment, the interbody implant 100 may have a compressive strength of between about 30 Kilo-Newtons and about 34 Kilo-Newtons measured with a load pressing the cephalad side 106 and the caudal side 108 towards each other. In another embodiment, the interbody implant 100 may have a compressive strength of between about 32 Kilo-Newtons and about 33 Kilo-Newtons measured with a load pressing the cephalad side 106 and the caudal side 108 towards each other. In another embodiment, the interbody implant 100 may have a compressive strength of between about 24 Kilo-Newtons and about 40 Kilo-Newtons measured with a load pressing the cephalad side 106 and the caudal side 108 towards each other. This larger range compressive strength may be accomplished for example by using pillars 142 having larger diameters than those in the illustrated embodiments.

In another example in one embodiment, the interbody implant 100 may have a density of between about 2 grams per centimeter cubed to about 2.5 grams per centimeter cubed. In another embodiment, the interbody implant 100 may have a density of between about 2.1 grams per centimeter cubed to about 2.4 grams per centimeter cubed. In another embodiment, the interbody implant 100 may have a density of between about 2.2 grams per centimeter cubed to about 2.3 grams per centimeter cubed.

In another example in one embodiment, the interbody implant 100 may have a stiffness of between about 31 Kilo-Newtons per millimeter and about 36 Kilo-Newtons per millimeter. In another embodiment, the interbody implant 100 may have a density of between about 32 Kilo-Newtons per millimeter and about 35 Kilo-Newtons per millimeter. In another o embodiment, the interbody implant 100 may have a density of between about 33 Kilo-Newtons per millimeter and about 34 Kilo-Newtons per millimeter.

FIGS. 1-8 illustrate that the mesh 124 may include pores 128 that extend all the way through the mesh 124 from one surface to an opposite surface. Such pores 128 may be referred to as through holes or through pores. In one embodiment, a plurality of pores 128 extend from the graft opening 120 to an external surface (one opposite the graft opening 120) of the mesh 124 or sidewall. Additionally, these figures illustrate that the plurality of pores 128 can vary in diameter based on a position (e.g., mesh position) of the pore 128 in the sidewall/mesh and a transition feature. In one embodiment, the transition feature may be a first locus 130 and/or a distance of a pore 128 in relation to the first locus 130 or transition feature. In certain embodiments, the transition feature may be a formulae that includes a distance of a pore 128 from a first locus 130 and a modifier. The modifier can be a natural number, a whole number, and/or a rational number.

In certain embodiments, the interbody implant may comprise an interbody implant 200 design specifically for use between the vertebrae of the other sections (e.g., thoracic or lumbar) of the spine. FIGS. 8-14 illustrate different views of an interbody implant 200, according to another embodiment. The interbody implant 200 may include many substantially similar components, parts, aspects, features, and attributes as the interbody implant 100 previously described. Consequently, such similar components are indicated in FIGS. 8-14 using the same reference numerals. Different components, parts, aspects, features, and attributes will have different reference numerals and will be discussed.

In certain embodiments, the interbody implant 200 may include a cephalad side 106 and/or caudal side 108 that includes one or more ridges 210. The ridges 210 may serve to engage with surfaces of vertebrae when the interbody implant 200 is deployed between vertebrae of a patient. The ridges 210 can provide a rough surface that engages with bone to prevent or mitigate movement and relocation of the interbody implant 200. The ridges 210 may have a variety of configurations, shapes, and sizes. The angles of the inclines on either side of each ridge may be uniform or varied, as needed. In certain embodiments, the ridges 210 may replace the frame 126 and/or frame members 124a-c. Alternatively, or in addition, the ridges 210 may be integrated with and configured to include a frame 126.

In certain embodiments, the interbody implant 200 may include one or more stabilization openings 220. The stabilization openings 220 may serve as a stabilization feature to facilitate proper deployment and positioning of the interbody implant 200 within a patient. For example, the interbody implant 200 may be used for a Transforaminal lumbar interbody fusion (TLIF) procedure between thoracic vertebrae. The larger vertebrae may use a larger interbody implant 200. The stabilization openings 220 may facilitate engagement, positioning, adjustment, and/or deployment of the interbody implant 200 between the larger vertebrae. In particular, the stabilization openings 220 may prevent twisting or other movement of the interbody implant 200 during deployment during a procedure.

In the illustrated embodiment, the stabilization openings 220 comprise an opening that extends between the anterior side 102 and the graft opening 120 and has a smooth internal wall. In certain embodiments, the stabilization openings 220 may receive pins or shafts that may extend from an inserter and engage with the stabilization openings 220. Together the stabilization openings 220 and pins or shafts may mitigate rotation of the interbody implant 200 during deployment. The stabilization openings 220 is another example of an implant structure that may be included in an interbody implant 100, 200. In certain embodiments, these implant structures may be the only structures of an interbody implant 100, 200 that are not made from the mesh 124. In certain embodiments, the interbody implant 200 may be fabricated using additive manufacturing.

Figure 9:
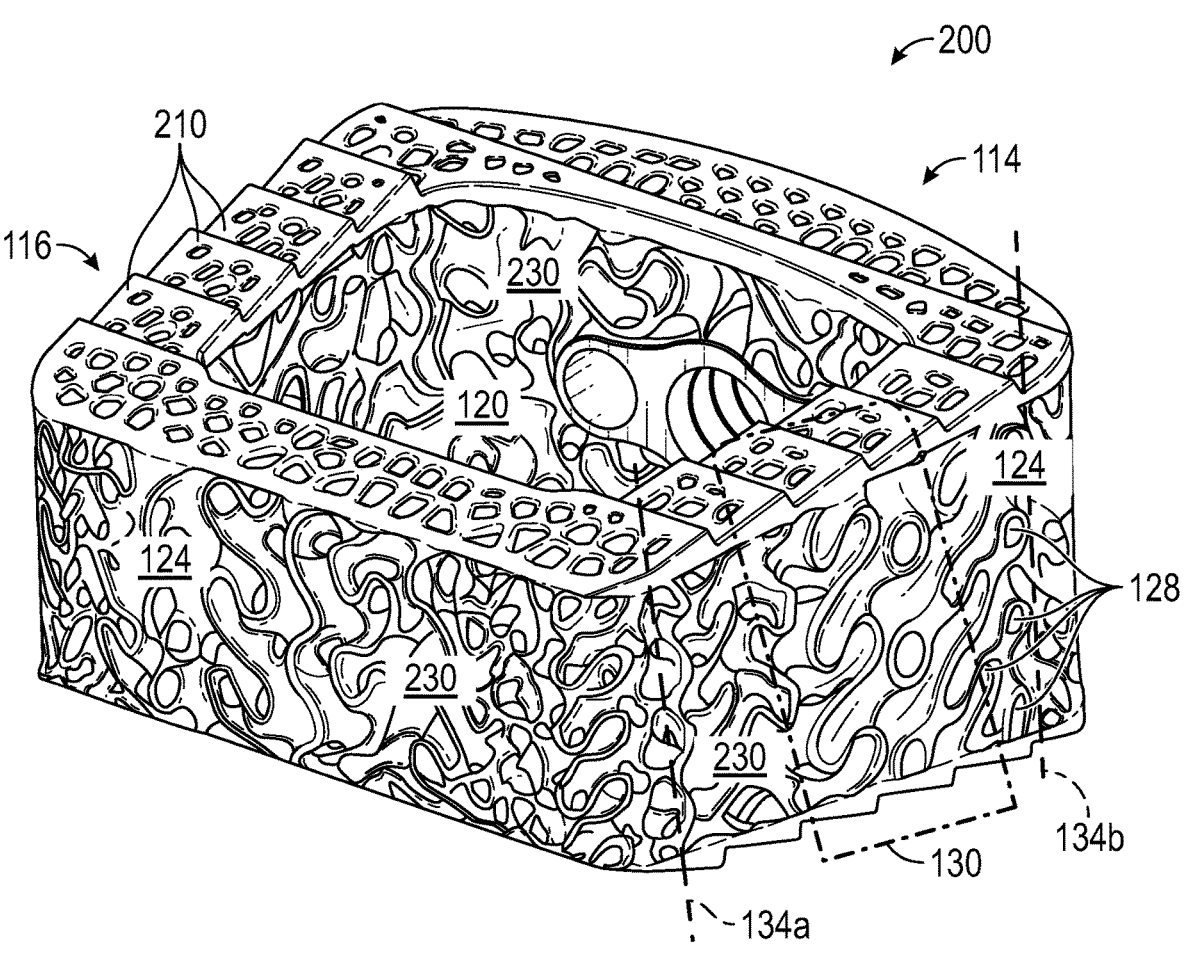
FIG. 9 is another perspective view of the interbody implant of FIG. 8 from a posterior direction, according to one embodiment.

FIG. 9 illustrates another way to characterize the components of the interbody implant 200. For example, the interbody implant 200 may be characterized as a cephalad side 106 and opposite caudal side 108 with a sidewall 230 that connects the cephalad side 106 to the caudal side 108 and circumscribes the graft opening 120. In such an embodiment/characterization, the sidewall 230 may form each of the sides of the interbody implant 200 (e.g., an anterior side 102, posterior side 104, right side 110, and left side 112). Advantageously, the sidewall 230 may comprise a single unitary structure. In addition, the sidewall 230 may be formed from the mesh 124 described above.

One aspect of both the interbody implant 100 and the interbody implant 200 is that the mesh 124 includes pores that have varying diameters. Those of skill in the art will appreciate that this varying of pore sizes/diameters can be done in a variety of ways including a pore configuration relationship between pore positions in the mesh 124 and a first locus 130. FIG. 9 illustrates yet another way to vary a pore configuration within the mesh 124. The mesh 124 may include a first locus 130 and a second locus 136. The pore sizes/diameters of the pores of the mesh may vary in diameter between the first locus 130 and the second locus 136.

FIG. 9 illustrates that the pore sizes in the mesh 124 may vary between a first locus 130 and one or more second loci 136*a,b*. In the embodiment of FIG. 9, the first locus 130 may be represented by an area of a dotted rectangle that covers an area of the sidewall 230. The second locus 136 is indicated a dashed line at one of the ends of a side, such as left side 112. The second locus 136 can be at an end of a side, such as right side 110 or left side 112 or at any point along the side. In certain embodiments, the pore sizes in the mesh 124 may vary between a first locus and two or more loci.

In certain embodiments, the mesh 124 may be configured to vary pore diameters as the pore's position relates to the first locus 130. In such an embodiment, the pore diameters may vary between a maximum desired pore diameter and a minimum desired pore diameter. Moving within the sidewall 230 away from the first locus 130 the pore diameter may increase or decrease depending on the type of embodiment that will be fabricated. In one embodiment, the maximum desired pore diameter is a first pore size, and the minimum desired pore diameter is a second pore size.

In one embodiment, the minimum desired pore diameter may be 100 micrometers and the maximum desired pore diameter may be 1000 micrometers. In another embodiment, the minimum desired pore diameter may be 200 micrometers and the maximum desired pore diameter may be 900 micrometers. In another embodiment, the minimum desired pore diameter may be 300 micrometers and the maximum desired pore diameter may be 600 micrometers. Advantageously, pore diameters in the mesh 124 are representative of the naturally occurring sizes of pores in cancellous bone. Providing a mesh 124 that is substantially similar to cancellous bone in porosity and pore size can facilitate new bone growth, on, around, and through the interbody implant. "Porosity" refers to a measure of how porous a material, object or structure is. Porosity can be expressed as a ratio of the volume of pores in an object to the total volume of the object. Porosity can be expressed as a percentage of the ratio of the volume of pores in an object to the total volume of the object. (Search "porosity" on wordhippo.com. WordHippo, 2022. Web. Modified. Accessed 28 Sep. 2022)

In certain embodiments, the pores within the mesh 124 may vary in pore diameter between 300 micrometers (microns) and 700 micrometers (microns). Furthermore, this variation may be engineered or configured such that views of the internal aspects of the graft opening 120 are visible using fluoroscopy imaging while still providing a desired level of load support and rigidity. In certain embodiments, the pores of a mesh 124 can vary based on a linear distance relationship between the pore and the locus 130, based on an exponential distance relationship between the pore and the locus 130, based on a quadratic distance relationship between the pore and the locus 130, or the like.

Advantageously, using a mesh 124 that is similar in size, shape, porosity, surface area, and volume to cancellous bone can provide a suitable framework for bone growth (on growth and/or ingrowth) such that a desired level of bone growth is achieved faster than has been available in the past. In the present disclosure, use of a mesh 124 for the interbody implant 100 and/or interbody implant 200 provides an increased amount of surface area for new bone and/or graft bone material to grow on. In various embodiments, in comparison to sides (e.g., anterior side 102, posterior side 104, cephalad side 106, caudal side 108, right side 110, and left side 112 or a sidewall 230) made from a solid material, embodiments of the mesh 124 disclosed herein has an increase of surface area of between 160% and 245% for an average increase in surface area of 204%. The increase in surface area can provide more locations for natural or bone graft bone growth. Similarly, in other embodiments, in comparison to sides (e.g., anterior side 102, posterior side 104, cephalad side 106, caudal side 108, right side 110, and left side 112 or a sidewall 230) made from a solid material, embodiments of the mesh 124 disclosed herein has an increase of surface area of between 51% and 55% for an average reduction in volume of the side(s) of 54%. The reduction in volume can enable more natural bone and bone graft to grow within a framework formed by the mesh 124.

Cancellous bone has a porosity that ranges from about 75% to about 80% and pore sizes that range from between about 300 microns and about 600 microns. Advantageously, the pore diameters of the embodiments of the present disclosure, such as the interbody implant 100 and/or interbody implant 200, ranges from 300 microns and 600 microns. Consequently, a majority of the pores of the interbody implant 100 and/or interbody implant 200 have sizes comparable to pores in cancellous bone.

The porosity of the interbody implant 100 and/or interbody implant 200 can range from between about 60% to about 75% depending on the size of the interbody implant. One factor that can influence the porosity of embodiments of the present disclosure, such as the interbody implant 100 and/or interbody implant 200, can be the number, size, shape, and/or positioning of the pillars 142. In certain embodiments, the pillars 142 may take up the same cross-sectional regardless of the size of the interbody implant. Consequently, larger implants can have a larger area and/or volume of mesh 124 which can translate into a higher porosity percentage.

Certain embodiments of the present disclosure, such as the interbody implant 100 and/or interbody implant 200, may include no pillars 142. Such embodiments have about 80% porosity regardless of implant size which substantially matches the porosity of cancellous bone. With a porosity that is comparable to, similar to, or substantially the same as cancellous bone the interbody implant provides enhanced osseointegration.

The mesh 124 for the interbody implant 100 and/or interbody implant 200 that has a varying pore diameter can facilitate imaging of a patient who in received the interbody implant. As a patient is healing and recovering from a surgical procedure that includes deployment of the interbody implant 100 and/or interbody implant 200 a surgeon or doctor may want to view progress of bone growth within (e.g., graft opening 120), through, and around, the interbody implant 100 and/or interbody implant 200. To view such progress, imaging technologies such as fluoroscopy may be used.

Fluoroscopy is a medical imaging technology that uses X-rays which tend to scatter when they contact metals such as titanium. In certain embodiments, the interbody implant 100 and/or interbody implant 200 may be manufactured from powdered titanium that fused together by a laser during additive manufacturing. Interbody implants 100,200 of solid titanium present a barrier to a surgeon using fluoroscopy to view progress of bone growth within the graft opening 120 of the implant.

Advantageously, embodiments of the implants 100,200 in the present disclosure include pores and specifically through pores that facilitate viewing bone growth activity within the graft opening 120. Further, certain embodiments of the present disclosure include interbody implants 100,200 having pores that vary in diameter as the pores are distributed along a side (e.g., right side 110 and/or left side 112). In certain embodiments, the pores near the middle of the side may be larger (e.g., 600 micrometers) than pores near the ends of the side.

The larger pores near the middle of the sides of an interbody implant 100,200 permit more x-rays to pass through the sides which then enhances the view of the inside of the graft opening 120 when a surgeon views the interbody implant 100,200 using fluoroscopy imaging.

Alternatively, or in addition, the mesh 124 may be configured to vary pore diameters as the pore's position relates to both the first locus 130 and the second locus 136. For example, the mesh 124 may include pores that are of a maximum diameter within the area of the first locus 130 and the pore diameters may then decrease as pores are formed moving towards the second locus 136. At a certain point the decrease in pore diameters may reach a minimum pore diameter (e.g., 300 micrometers) and pores from that mesh position on towards a distal end 116 or proximal end 114 may have the minimum pore diameter. Of course, the variation may be done in reverse from a minimum pore diameter to a maximum pore diameter based on a mesh position relative to the first locus 130, the second locus 136, and/or both the first locus 130 and the second locus 136.

Figure 10:
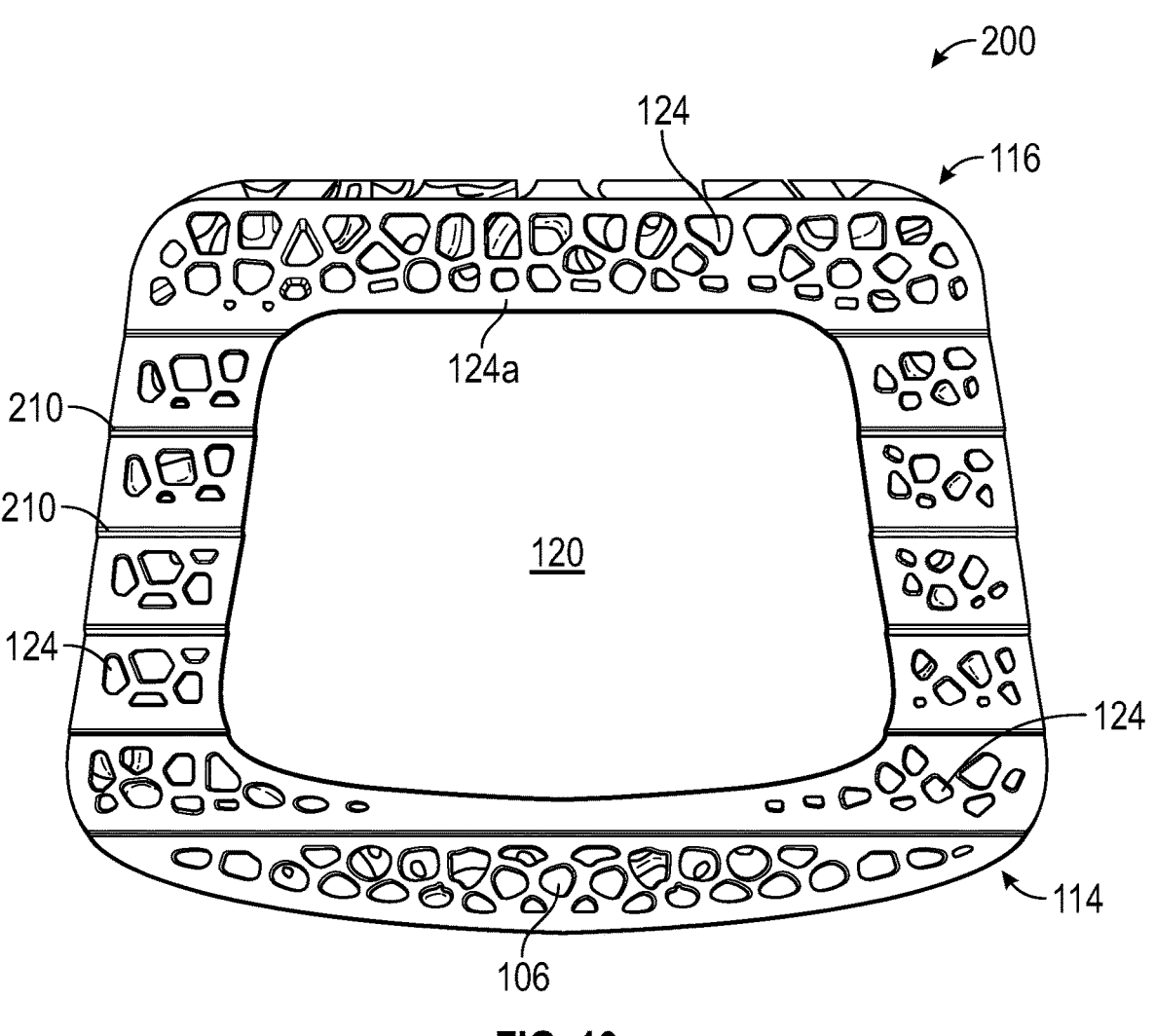
FIG. 10 is a top view of the interbody implant of FIG. 8, according to one embodiment.

FIG. 10 illustrates a top view with like components indicated using the same numbers as the embodiment illustrated in FIGS. 1-13. The bottom of the interbody implant 200 may be substantially similar to the top view.

Figure 11:
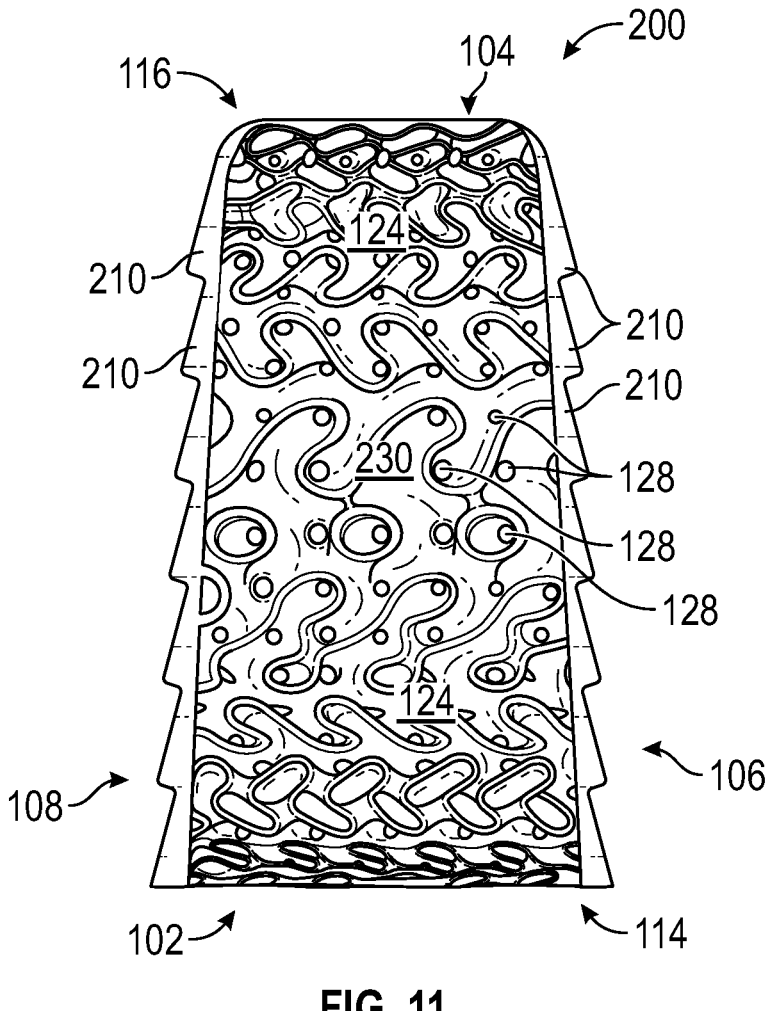
FIG. 11 is a left view of the interbody implant of FIG. 8, according to one embodiment.

FIG. 11 illustrates a side view with like components indicated using the same numbers as the embodiment illustrated in FIGS. 1-13. The sidewall 230 on one side (e.g., left or right) is illustrated. The opposite side of the interbody implant 200 may be substantially similar to the side shown. FIG. 11 illustrates that in certain embodiments, The cephalad side 106 and/or the caudal side 108 may each have a slope of the side between the proximal end 114 and the distal end 116. Alternatively, or in addition, in other embodiments, the cephalad side 106 may be parallel to the caudal side 108. In certain embodiments, the slope may relate to the Lordotic angle and may be 7 degrees, 9 degrees or 10 degrees. In FIG. 11 the slope is 7 degrees.

Figure 12:
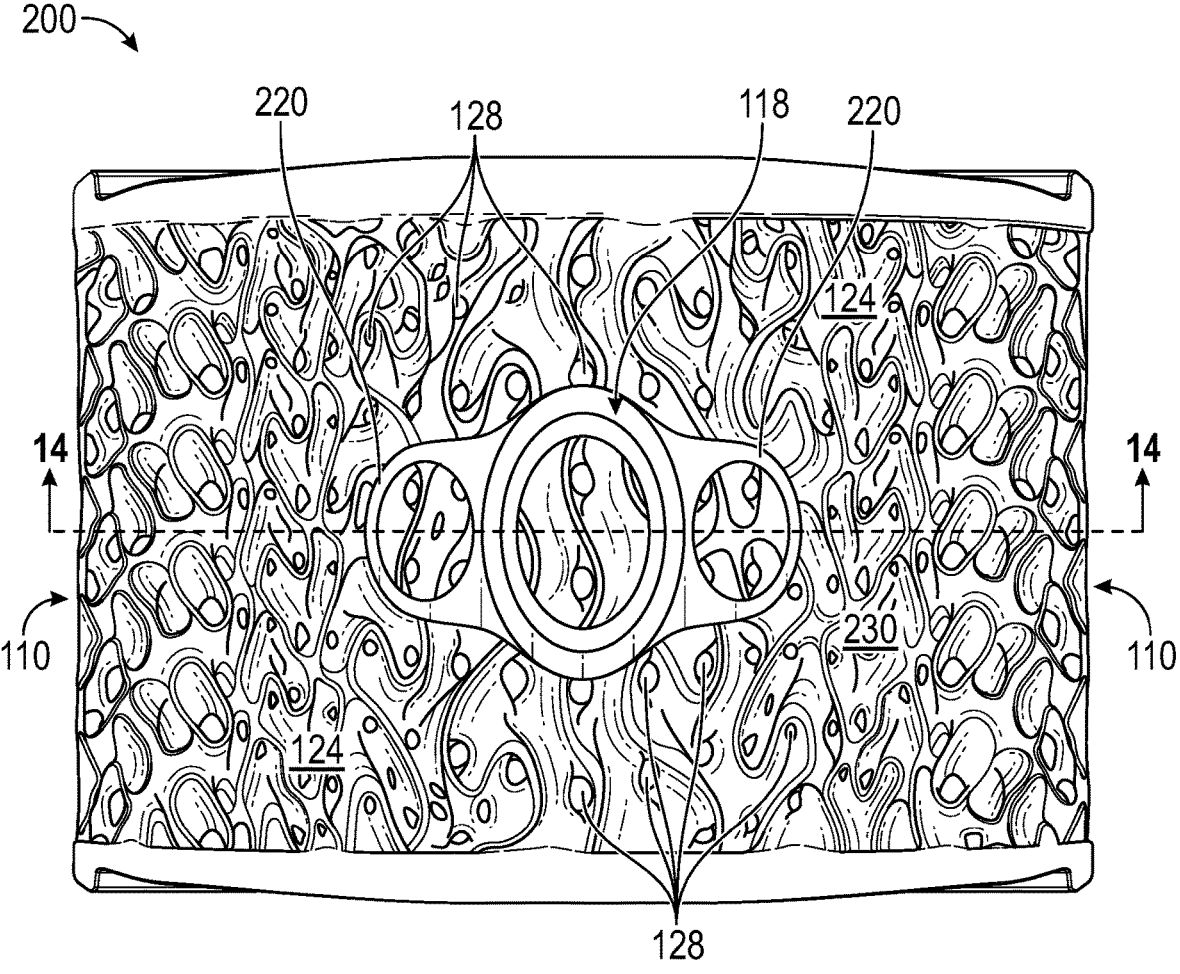
FIG. 12 is a front view of the interbody implant of FIG. 8, according to one embodiment.

FIG. 12 illustrates a front view with like components indicated using the same numbers as the embodiment illustrated in FIGS. 1-13. FIG. 12 includes a cross-section line 14-14 which indicates where the cross-section is taken for FIG. 14.

Figure 13:
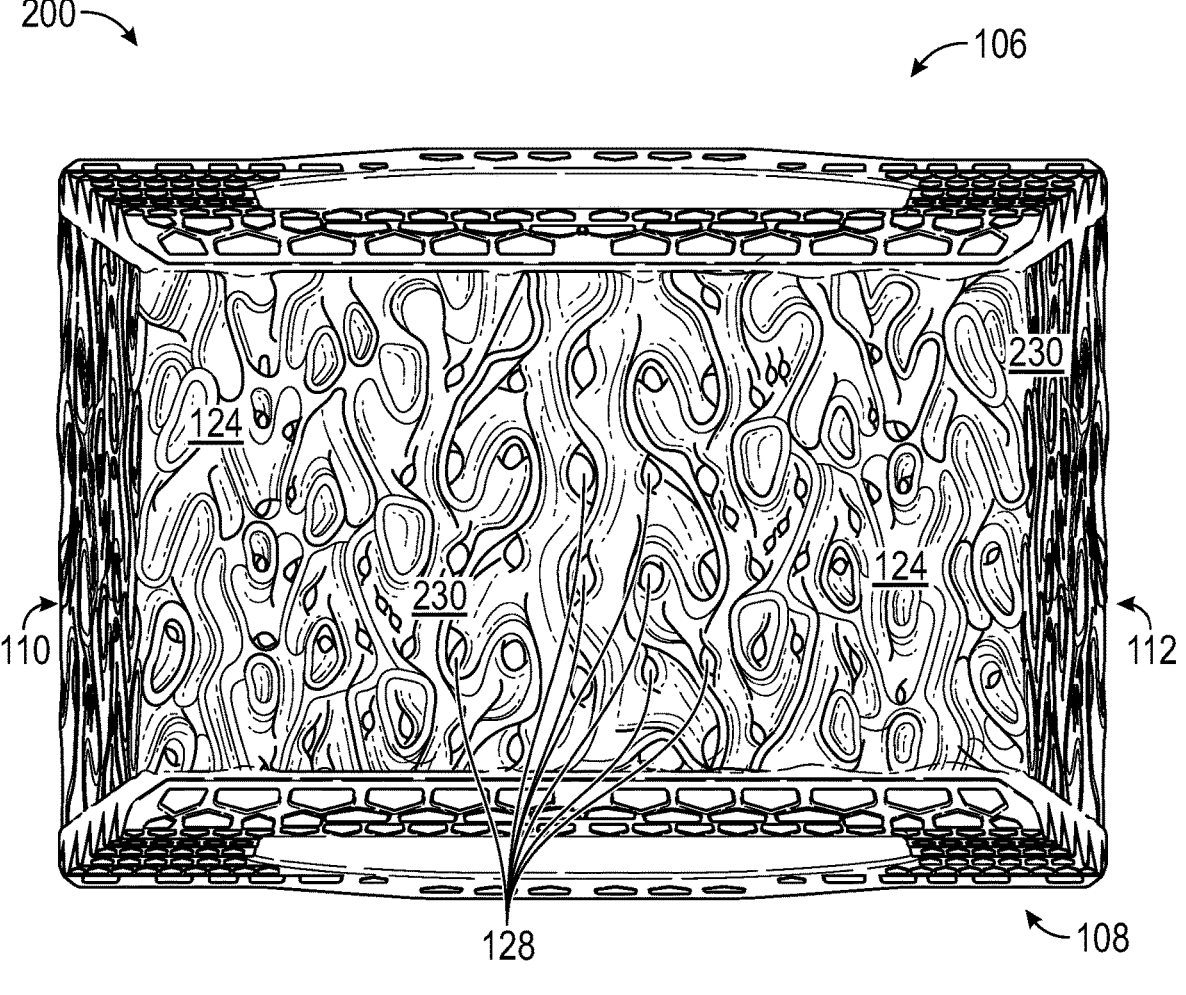
FIG. 13 is a back view of the interbody implant of FIG. 8, according to one embodiment.

FIG. 13 illustrates a rear view with like components indicated using the same numbers as the embodiment illustrated in FIGS. 1-13. FIG. 13 illustrates that in this embodiment the right sidewall 230 can taper as the sidewall 230 approaches the posterior side 104 (the distal end 116). Consequently, the back side of the sidewall 230 may be smaller than the front side.

Figure 14:
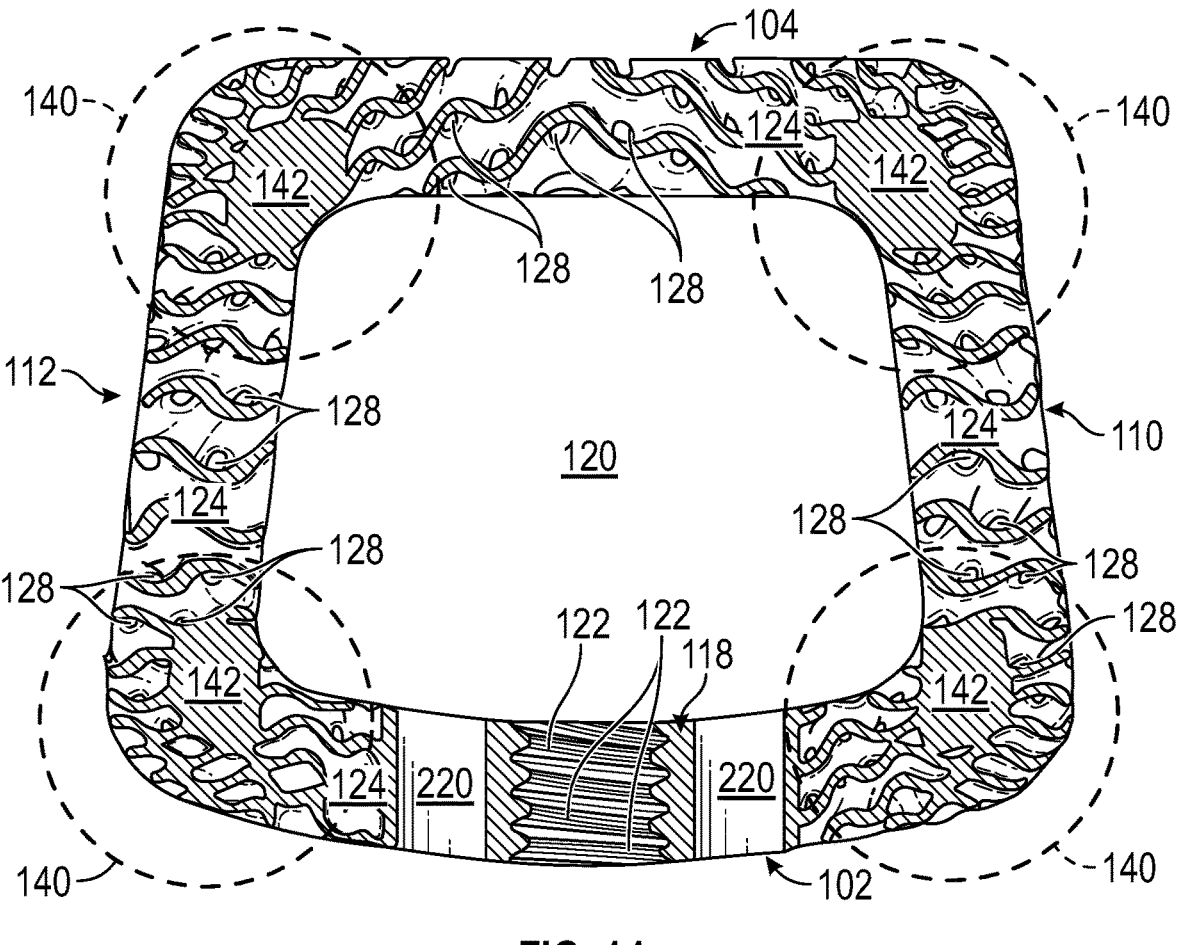
FIG. 14 is a section view of the interbody implant of FIG. 12 taken through line 14-14, according to one embodiment.

FIG. 14 illustrates section view of the interbody implant 200 of FIG. 12 taken through line 14-14, according to one embodiment with like components indicated using the same numbers as the embodiment illustrated in FIGS. 1-13. The interbody implant 200 includes the stabilization openings 220. In the illustrated embodiment, the interbody implant 200 may include corners 140. In other embodiments, the interbody implant 200 may include a sidewall 230 configured such that the graft opening 120 is created and the interbody implant 200 includes no corners. For example, the section illustrated in FIG. 14 may be a circle or circular.

FIG. 15 illustrates one example of a method 1500 for making an implant that has variable size pores, pores having variable size diameters. Referring to FIGS. 15 and 16-22, the method 1500 starts with a user, such as a surgeon, designer, engineer, technician, or the like generating 1502 a mesh model 1600 (See FIG. 16) for an implant. In certain embodiments, the mesh model 1600 may include one or more implant features such as a frame 126, pillar(s) 142, an engagement feature 118, stabilization openings 220, or the like.

Figure 16:
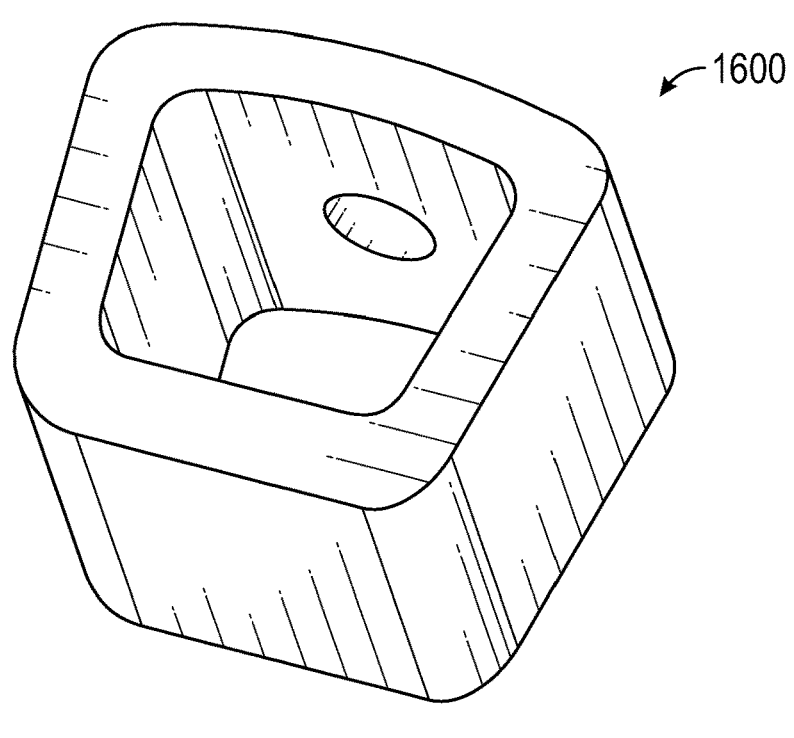
FIG. 16 illustrates one example of a mesh model that can be used with the method described in relation to FIG. 15.

A variety of tools, techniques, and/or methods may be used to generate the mesh model 1600. The mesh model 1600 may have a visual representation as shown in FIG. 16 or may be represented by mathematical equations and configuration data. Examples of tools that may be used to practice one or more aspects of the disclosed method 1500 may include various Computer Aided Design (CAD) tools, Computer Aided Manufacturing (CAM) tools, Computer Aided Engineering (CAE) tools, 3D solid modeling tools, mesh generating software, and the like. Examples of such tools include but are not limited to nTopology, AutoDesk, AutoCAD, SolidWorks, Blender, WorldCAT, Open CAS-CADE, and Rhinoceros 3D. In certain embodiments, the mesh model 1600 represents where in an implant a mesh is desired.

Next, a user determines 1504 a transition feature. In one embodiment, the transition feature factors into or plays a part in a pore configuration relationship between the mesh model 1600 and the transition feature. In one embodiment, a transition feature is a feature that is part of the pore configuration relationship and together the transition feature and pore configuration relationship define how the pore configuration relationship will be realized within the mesh once the mesh is generated. Since a pore configuration relationship is a relationship, or association, between an attribute, feature, or configuration aspect of a pore relative to one or more references and a determinable attribute. The transition feature may represent and define the configuration aspect of the pores that may be altered, one or more references for the alteration, and the determinable attribute.

In one embodiment, the pore configuration relationship includes a modification of a mesh pore size for the mesh 124 based on a distance between a mesh position within the mesh model and an intersection of the mesh model with the transition model. In certain embodiments, this modification may include decreasing pore diameter size for pores 128 of the mesh 124 from the first pore size down to the second pore size based on an increasing distance between a mesh position within the mesh model and an intersection of the mesh model with the transition model.

In one embodiment, the transition feature may include a transition model. In one example, the transition feature may define the configuration aspect of the pores to be pore diameter and the one or more references to be points within a transition model (e.g., one or more loci) and the determinable attribute to be a distance between the pore and one or more points within a transition model.

In addition, the transition feature may also include a first pore size and a second pore size. The first pore size and second pore size may serve as an upper bound pore diameter size and/or a lower bound pore diameter size for pore sizes to range between within a particular pore configuration relationship. The pore configuration relationship may include a modification of a mesh pore size for the mesh based on a distance between a mesh position within a mesh model and an intersection of the mesh model with the transition model.

Figure 17:
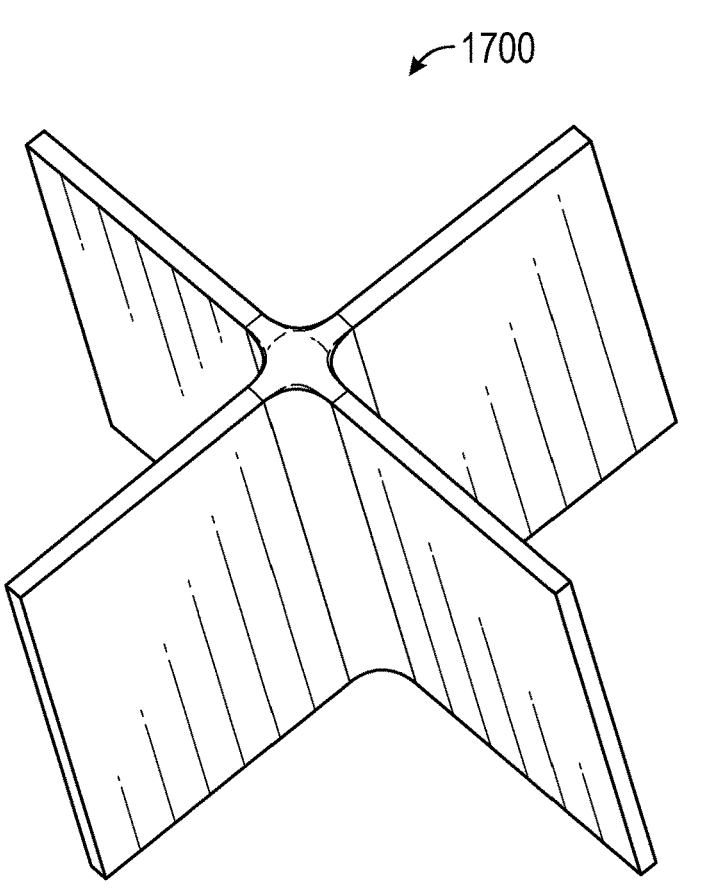
FIG. 17 illustrates one example of a transition model that can be used with the method described in relation to FIG. 15.

In one embodiment, the transition feature includes a transition model 1700. FIG. 17 illustrates one example of a transition model 1700. The transition model 1700 can be of any size, shape, dimension, or configuration. In the illustrated example, the transition model 1700 is a shaped as a three-dimensional 'X' shape (the transition model 1700 may have a longitudinal cross-section that is in the shape of a letter X). The legs of the X may extend from a single point at right angles. In certain embodiments, one or more legs of the X may intersect with the mesh model 1600 at a midpoint of four sides of the mesh model 1600. The transition model 1700 may have any shape (an oval shape, a letter "T" shape, a letter "L" shape, a rectangular prism, a cylinder, a cone, a sphere, a cube, a cuboid, a torus, a polyhedron, and the like).

Figure 18:
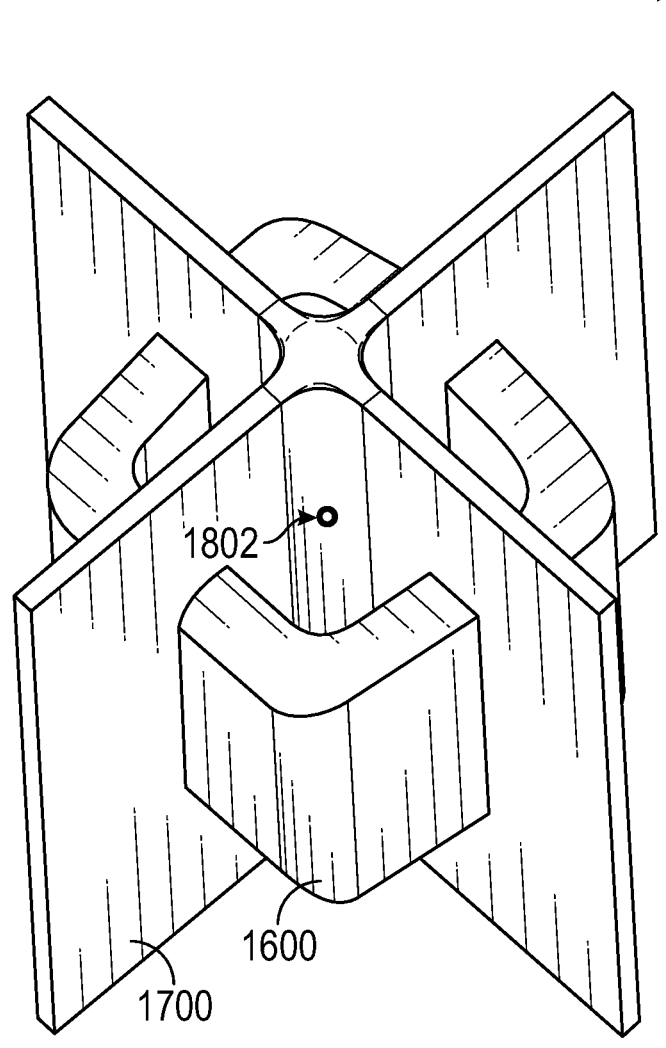
FIG. 18 illustrates one example of a revised model that can be used with the method described in relation to FIG. 15.

Next, a user generates 1506 a revised model by applying the transition feature to the mesh model 1600. FIG. 18 illustrates visually how this may be done. For example, a user may combine the mesh model 1600 and a transition model 1700 to form a new model, a revised model 1800. First, a user may cause the transition model 1700 to use a common origin 1802 with the mesh model 1600. Placing both models at a common origin 1802 results in one or more parts of the transition model 1700 intersecting with one or more parts of the mesh model 1600. In one embodiment, one or more legs of an "X" shaped transition model 1700 may intersect the mesh model 1600 at a midpoint of each of four sides of the mesh model 1600.

In certain embodiments, the pore configuration relationship may be based at least in part on where portions of the mesh model 1600 intersect with the transition model 1700. For example, in one embodiment, the pore configuration relationship may define the area where the mesh model 1600 and the transition model 1700 intersect as an area for pores of a mesh to have a maximum pore size. Such an intersection may be a first locus 130 that is used to generate a mesh 124. Furthermore, the pore configuration relationship may define that pores formed in the mesh model 1600 will have a pore diameter that is dependent on a distance between the pore, or mesh position, for the pore in the mesh model 1600 and the next closest point of intersection between the mesh model 1600 and the transition model 1700.

This dependency can be defined using various criteria. In one embodiment, the dependency is defined such that the further away from the point of intersection between the mesh model 1600 and the transition model 1700 the smaller the pore diameter will be. This dependency may continue until the pore diameter has reached a minimum pore diameter or a pore diameter so small that it is not practical to fabricate. With this example, the pore diameters in the mesh model 1600 will be at a maximum pore diameter where the mesh model 1600 and transition model 1700 intersect and transition down to a minimum pore diameter as pores are formed in the mesh model 1600 moving from the area of intersection to the corners. In one embodiment, the pore configuration relationship may include a modification of a mesh pore size based on a distance between a mesh position (a location within a mesh) and an intersection of the mesh model 1600 and the transition model 1700. In certain embodiments, this modification may be implemented using a ramp operation that facilitates the desired modification based on the criteria defined by a user. In another embodiment, the pore configuration relationship may include a modification of a pore shape.

Figure 19:
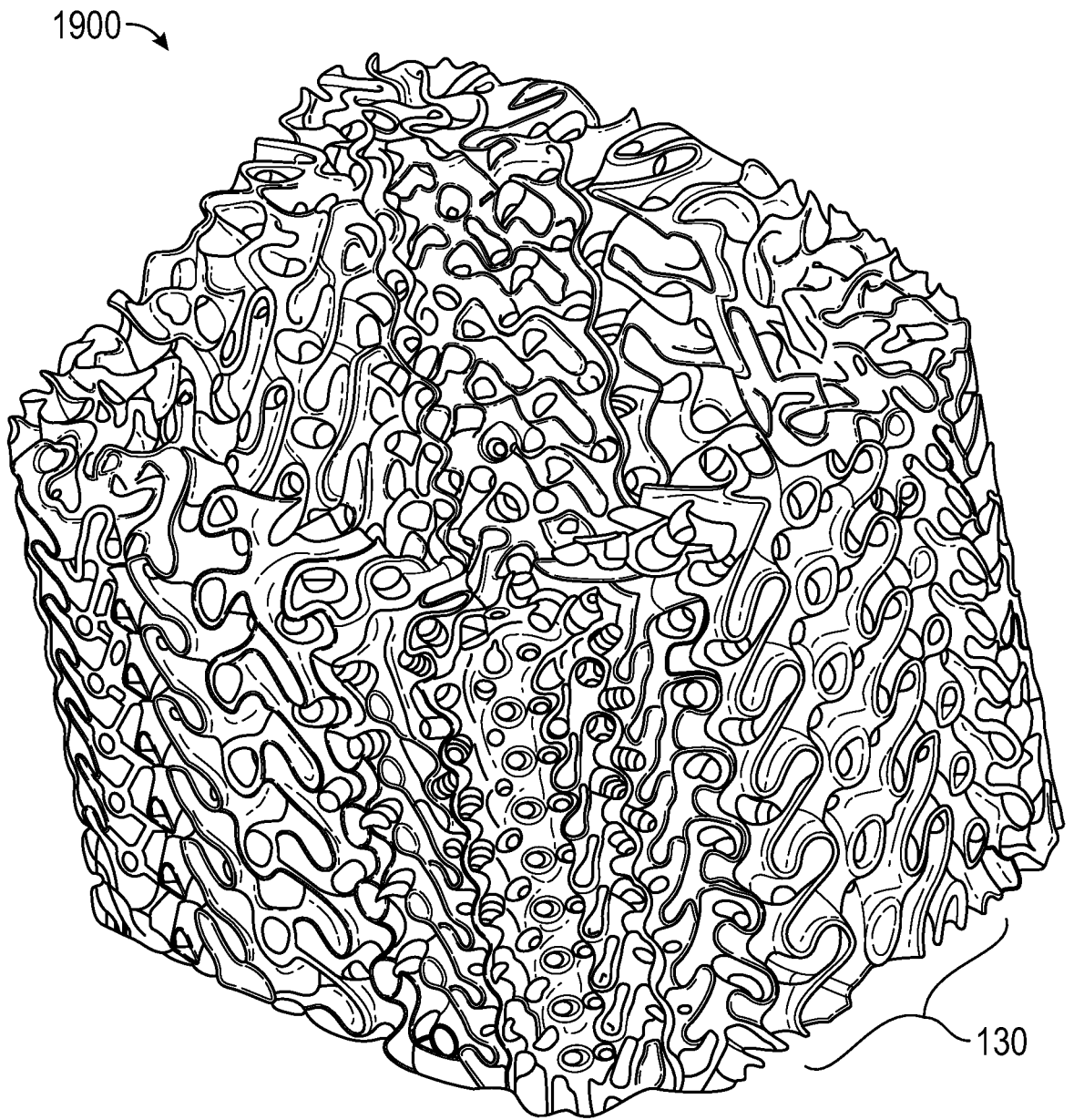
FIG. 19 illustrates one example of a mesh that can be used with the method described in relation to FIG. 15.

Next, a user generates 1508 a mesh 1900 bounded by the revised model 1800. The mesh includes pores of different configurations (e.g., pore diameters, pore shapes, based on mesh position relative to a first locus 130 and/or a second locus 136, etc.). FIG. 19 illustrates visually a result from this step. This step may be accomplished in a variety of ways.

In one example, a user may operate an aspect of a software tool that generates a model, specifically, a mesh 1900 based on the revised model 1800 and/or a pore configuration relationship that includes a transition feature. In one embodiment, the transition feature is a modifier for a formula, a modifier that changes based on how far a mesh position is from an intersection of the transition feature and the sidewall (e.g., a wall of a mesh model 1600).

The tool may map a mesh structure onto the mesh model 1600 and change characteristics or configuration settings of the mesh based on a pore configuration relationship and/or the transition model 1700. Since the transition model 1700 does not define areas for including the mesh structure, and the mesh model 1600 does define areas for including a mesh structure, the mesh 124 takes the form of the mesh model 1600. In addition, the tool applies the transition feature such that pore sizes are modified as pores are formed moving from a corner to where the transition model 1700 intersected the mesh model 1600. Specifically, in the illustrated embodiment, the pore size decreases as pores 128 are defined from the middle of a side towards the corners. FIG. 19 illustrates that a first locus 130 may exist where the transition model 1700 intersected with the mesh model 1600. Advantageously, the pores of the mesh 1900 comprise through pores.

Those of skill in the art will recognize that size, shape, and configuration of the transition feature can be varied in other embodiments to produce meshes that have a variety of different pore configurations, including diameter sizes. In certain embodiments, the transition feature may include a transition model 1700. In the illustrated embodiment, the transition model 1700 may extend both above and below a top side and an opposite bottom side of the mesh model 1600. This may result in the pore diameter size changes being applied for a side of the mesh model 1600 between the top side and opposite bottom side. However, those of skill in the art will recognize that other transition features and/or transition models 1700 having different shapes, sizes, configurations, orientations, and/or points of origin in relation to the mesh model 1600 can be used to generate a variety of different embodiments that have varied pore configurations, such as pore diameter size within an implant.

For example, in one embodiment the transition model 1700 may be a rectangular prism with a common origin with the mesh model 1600. The rectangular prism may extend through and intersect a side or sidewall of the mesh model 1600. However, the height of the rectangular prism may be less than that of the sides of the mesh model 1600. If the transition feature in this example is the same as that illustrated in relation to FIGS. 16-19, the pores of the mesh 1900 would be larger where the rectangular prism intercepts a wall or side of the mesh model 1600 but not in the area above or below rectangular prism on the wall where there is no intersection. In this manner, the rectangular prism can be used to generate a mesh 1900 that includes a radiolucent "window" of pores that have a different diameter or other configuration parameter.

Next, a user generates 1510 an implant model based on the mesh 1900. Finally, an implant is fabricated 1512 based on the implant model by way of additive manufacturing. In one embodiment, generating the implant model may include mapping one or more implant structures onto the mesh 1900. For example, a user may combine a model of an engagement feature, one or more pillars, and one or more stabilization openings with the mesh 1900. These implant structures may be positioned in locations that correspond to the embodiments of implants described herein, interbody implant 100 and/or interbody implant 200.

Figure 20:
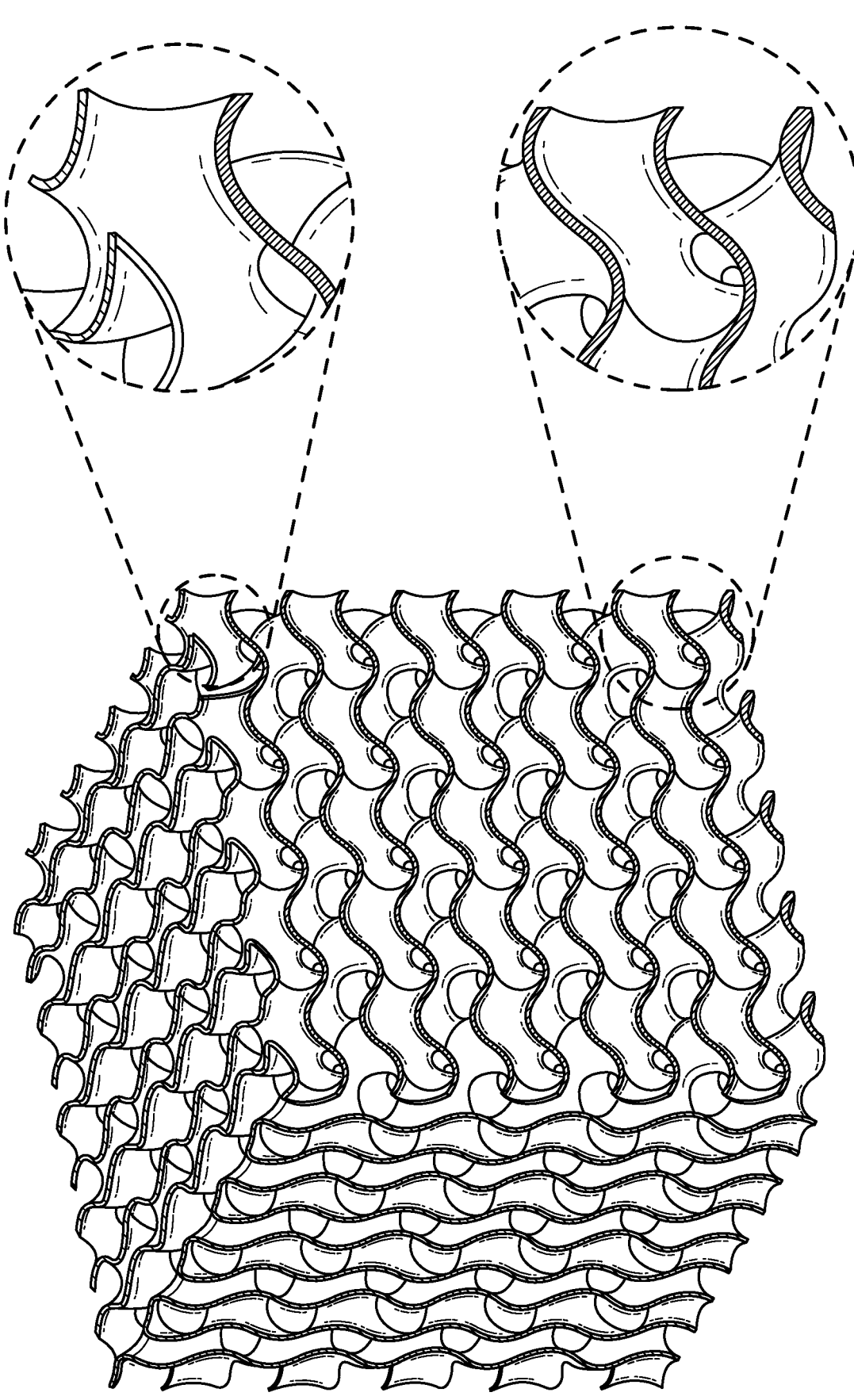
FIG. 20 illustrates one example of a gyroid field that can be used with the method described in relation to FIG. 15.

FIG. 20 illustrates one example of a gyroid field that can be used with the method described in relation to FIG. 15. In one embodiment, generation of a gyroid field may be used as part of the step of generating 1508 a mesh 1900 bounded by the revised model 1800. One or more aspects of generating 1508 the mesh 1900 may be performed using various Computer Aided Design (CAD) tools, Computer Aided Manufacturing (CAM) tools, Computer Aided Engineering (CAE) tools, 3D solid modeling tools, mesh generating software, and the like.

A gyroid is a type of infinitely connected surface that Alan Schoen discovered in 1970. Specifically, this surface is a type of triply periodic minimal surface (TPMS) and can be generated using a mesh generating software tool or feature of a CAD/CAM/CAE tool. Advantageously, a gyroid surface has a high surface area. The present disclosure applies the features, concepts and benefits of the gyroid surface type to generate 1508 a mesh 1900 bounded by the revised model 1800.

First, a user may define a triply periodic minimal surface (TPMS) field. FIG. 20 illustrates a particular type of TPMS field. In one embodiment, the TPMS field is a gyroid type TPMS field. The gyroid TPMS field is shown as a grey area because of the complexity of the surface and because no other models are present in the field to give the surface form or shape. In the illustrated example, the gyroid TPMS field is unbounded and therefore extends beyond the field of view of the drawing.

Figure 21:
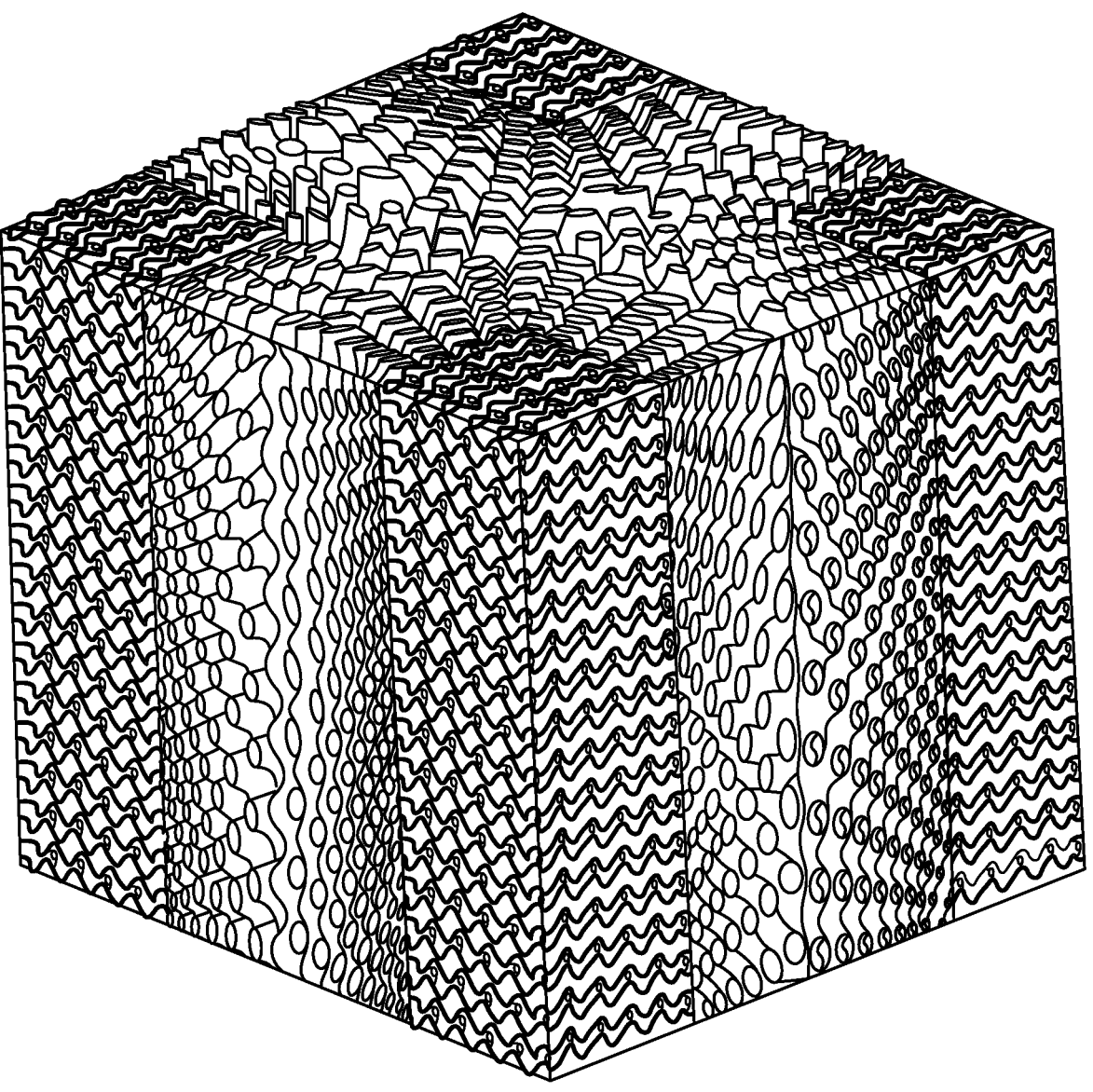
FIG. 21 illustrates one example of a TPMS field in relation to a transition feature that can be used with the method described in relation to FIG. 15.
Figure 22:
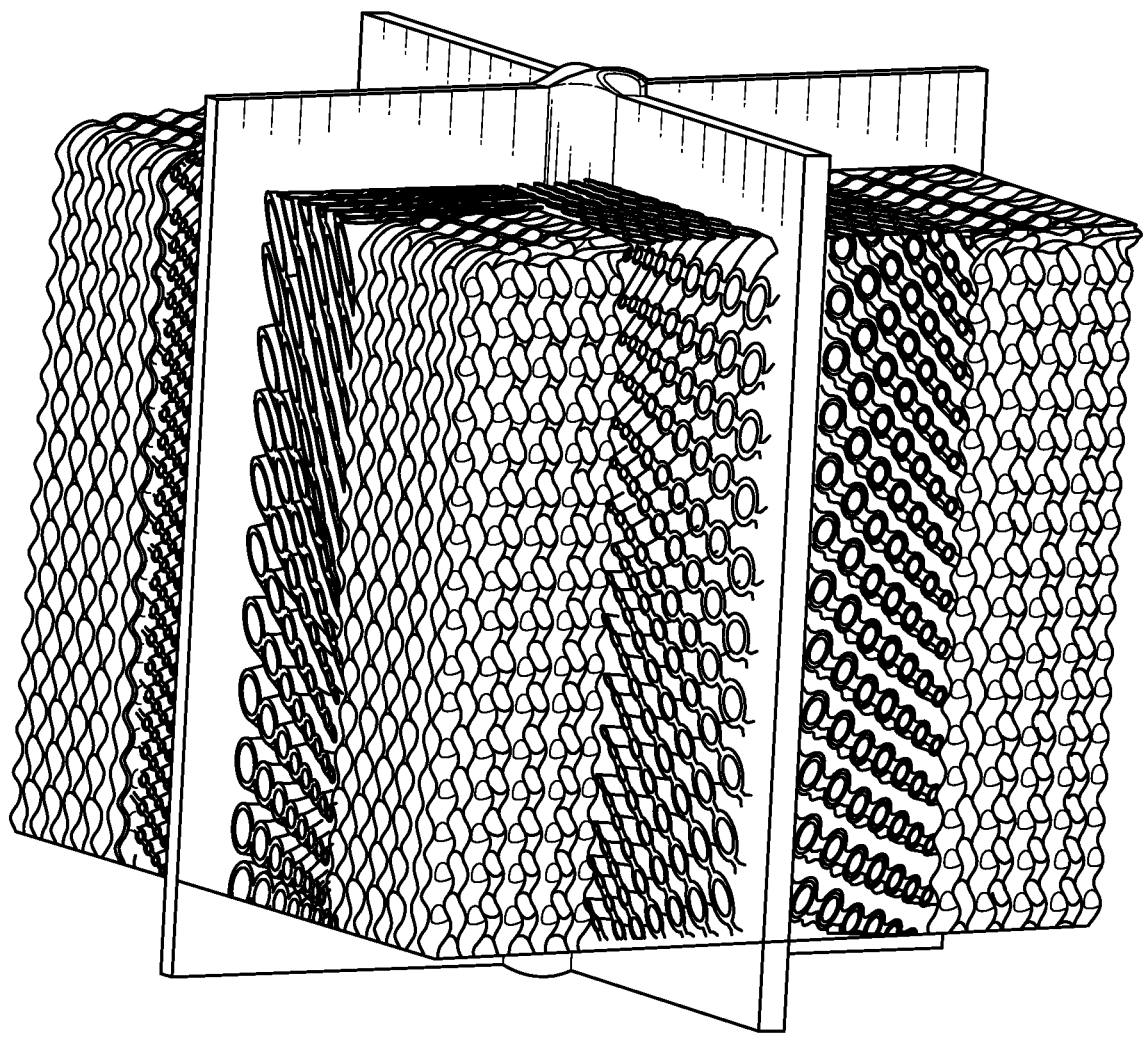
FIG. 22 illustrates one example of a TPMS field in relation to a transition feature that can be used with the method described in relation to FIG. 15.

FIG. 21 illustrates an example of a TPMS field in relation to a transition feature that can be used with the method described in relation to FIG. 15. The transition feature imposes some constraints on the gyroid TPMS field that can be visualized with FIG. 21. FIG. 21 illustrates that due to the pore configuration relationship of a transition feature, pores of a mesh surface within the gyroid TPMS field can have a different diameter size as the pores are positioned in relation to the transition feature (or a model of the transition feature; transition model 1700). The mesh surface within the gyroid TPMS field may form the mesh in an interbody implant. As described in more detail below, the mesh surface may be volumized. Advantageously, the mesh includes pores that vary in diameter based on a position of each pore in relation to a first locus. The pore diameters may vary between a maximum pore size and a minimum pore size. FIG. 22 illustrates one example of a gyroid TPMS field in relation to a transition model 1700 of a transition feature that can be used with the method described in relation to FIG. 15.

Figure 23:
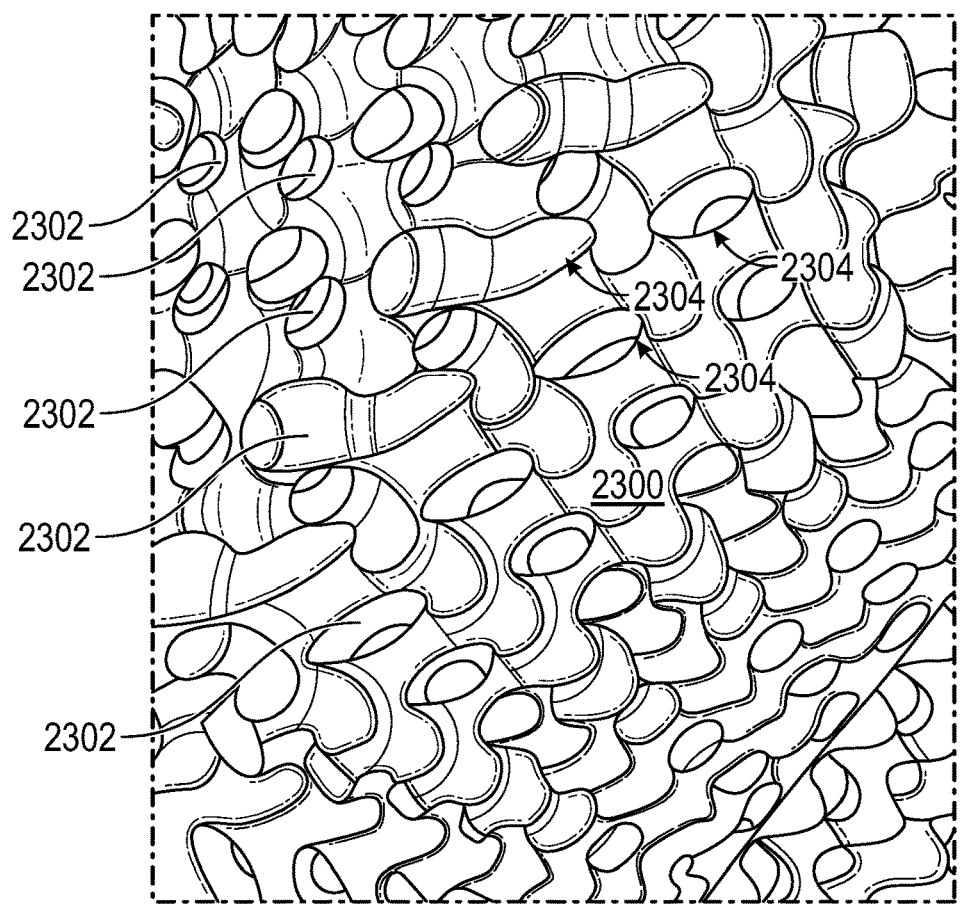
FIG. 23 illustrates one example of a TPMS mesh surface that can be used with the method described in relation to FIG. 15.

Next, a user can map the revised model 1800 into the TPMS field to generate a mesh surface. The mesh surface (also referred to as a TPMS mesh surface in certain embodiments) is bounded by the revised model 1800. Advantageously, the mesh surface 2300 includes pores. FIG. 23 illustrates one example of a TPMS mesh surface 2300 that can be used with the method described in relation to FIG. 15.

Figure 24:
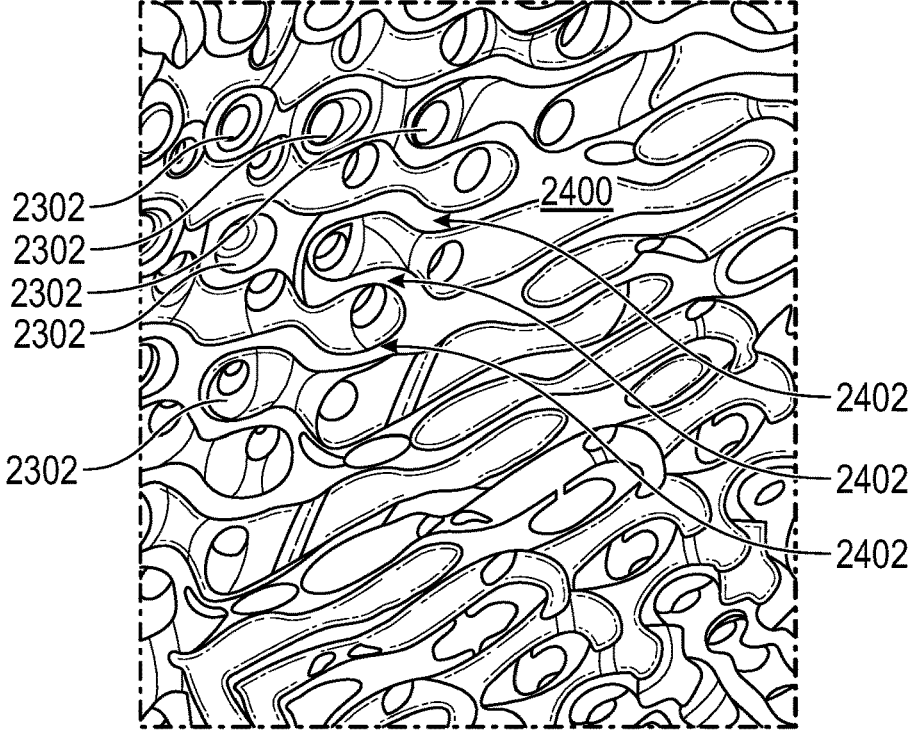
FIG. 24 illustrates one example of a volumized TPMS mesh surface that can be used with the method described in relation to FIG. 15.

Referring to FIG. 23, the TPMS mesh surface 2300 is three-dimensional however at this stage the TPMS mesh surface 2300 is a single surface, without structure or form beyond being a surface of minimal thickness. Consequently, a user may volumize a generated mesh surface, such as the TPMS mesh surface 2300, to generate volumized mesh surface 2400 which is used to generate a mesh 1900 bounded by the revised model 1800. Comparing FIGS. 23 and 24 one can see that lines 2304 between pores 2302 in FIG. 23 are replaced with a two dimensional wall 2402 between the pores 2302 in FIG. 24. Volumizing is the process of forming the two dimensional wall 2402 between the pores 2302 from the lines 2304 between pores 2302 in a mesh surface.

Figure 25:
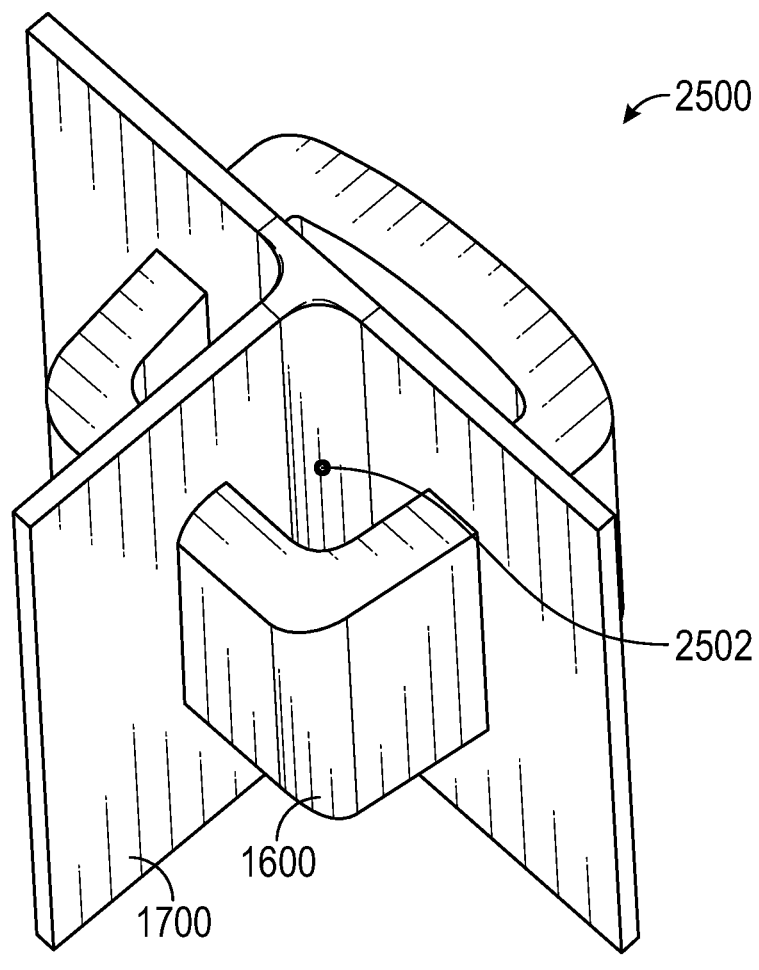
FIG. 25 illustrates another example of a revised model that can be used with the method described in relation to FIG. 15.

FIG. 25 illustrates one example of generating a revised model 2500 by applying a transition feature to the mesh model 1600 where the transition feature has a different three dimensional shape. FIG. 25 illustrates visually how this may be done. The transition model 2510 may be generated based on an alternative transition feature.

In one example, a user may combine the mesh model 1600 and the transition model 2510 to form a new model, the revised model 2500. First, a user may cause the transition model 2510 to use a common origin 2502 with the mesh model 1600. Placing both models at a common origin 2502 results in one or more parts of the transition model 2510 intersecting with one or more parts of the mesh model 1600. In one embodiment, the transition model 2510 may be shaped like a capital "T". Two arms of the "T" may intersect the mesh model 1600 at a midpoint of each of opposite sides of the mesh model 1600. For example, one arm may intersect a left side of the mesh model 1600 and another arm may intersect a right side of the mesh model 1600. A base of the "T" may intersect the mesh model 1600 at a midpoint of a posterior side of the mesh model 1600. Later in the process, when the revised model 2500 is used to generate a mesh and/or walls/sides or a sidewall of an interbody implant, the areas of intersection of the transition model 2510 can form radiolucent windows 134; one window in a right side 110, one window in a left side 112, and one window in a posterior side 104. In this manner, some but not all sides of a interbody implant can include a radiolucent window 134.

As used herein, an "opening" refers to a gap, a hole, an aperture, a space or recess in a structure, a void in a structure, or the like. In certain embodiments, an opening can refer to a structure configured specifically for receiving something and/or for allowing access. In certain embodiments, an opening can pass through a structure. In other embodiments, an opening can exist within a structure but not pass through the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape.

As used herein, a "pore" refers to a type of opening. In certain embodiments, a pore is an opening configured to facilitate passage of a gas, liquid, or other type of particle through the structure that includes the pore. In certain embodiments, a structure may include a plurality of pores. In certain embodiments, a pore can exist within a structure but not pass through the structure. Such pores are referred to herein as "dead-end pores." Alternatively, or in addition, a pore can exist within a structure that passes through the structure. Such pores are referred to herein as "through pores" because they permit passage of a gas, liquid, or other type of particle through the structure that includes the pore.

As used herein, a "graft" and/or "bone graft" refers to a surgical procedure to move tissue from one site to another on the body, or from another creature, without bringing its own blood supply with the tissue. Instead, a new blood supply grows in after the tissue is placed. A similar technique where tissue is transferred with the blood supply intact is called a flap. (Search 'Graft (surgery)' on Wikipedia.com Apr. 21, 2021. Modified. Accessed Aug. 30, 2021.) "Graft" and/or "bone graft" may also be used to refer to the tissue and/or synthetic composition used for a graft surgical procedure.

Bone grafting is a surgical procedure that replaces missing bone in order to repair bone fractures. Bone generally has the ability to regenerate completely but may require a small fracture space and/or a scaffold to do so. Bone grafts may be autologous (bone harvested from the patient's own body, often from the iliac crest), allograft (cadaveric bone usually obtained from a bone bank), or synthetic (often made of hydroxyapatite or other naturally occurring and biocompatible substances) with similar mechanical properties to bone. Generally, bone grafts are expected to be reabsorbed and replaced as natural bone heals over a few months' time. (Search 'Bone Grafting' on Wikipedia.com Apr. 21, 2021. Modified. Accessed Aug. 30, 2021.) Certain grafts may include a combination of autograft, isograft, allograft, xenograft, and/or synthetic materials in a single bone graft composition. An example of such a compositions, include but is not limited to, Demineralized bone matrix (DBM). Bone graft compositions may include bone morphogenetic proteins (BMPs).

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities.

Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Fluoroscopy is an imaging technique that uses X-rays to obtain real-time moving images of the interior of an object. In its primary application of medical imaging, a fluoroscope allows a physician to see the internal structure and function of a patient, so that the pumping action of the heart or the motion of swallowing, for example, can be watched. This is useful for both diagnosis and therapy and occurs in general radiology, interventional radiology, and image-guided surgery. (Search "medical imaging" on Wikipedia.com Jul. 14, 2021. CC-BY-SA 3.0 Modified. Accessed Sep. 1, 2021.)

Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. These technologies may be considered forms of medical imaging in certain disciplines. (Search "medical imaging" on Wikipedia.com Jun. 16, 2021. CC-BY-SA 3.0 Modified. Accessed Jun. 23, 2021.)

As used herein, a "fixation" refers to an apparatus, instrument, structure, device, component, member, system, assembly, step, process, or module structured, organized, configured, designed, arranged, or engineered to connect two structures either permanently or temporarily. The structures may one or the other or both manmade and/or biological tissues, hard tissues such as bones, teeth or the like, soft tissues such as ligament, cartilage, tendon, or the like. Typically, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

As used herein, "implant" refers to a medical device manufactured to replace a missing biological structure, support a damaged biological structure, or enhance an existing biological structure. Medical implants are manmade devices. The surface of implants that contact the body may be made of, or include a biomedical material such as titanium, silicone, or apatite depending on what is the most functional. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants are used to treat bone fractures, osteoarthritis, scoliosis, spinal stenosis, and chronic pain. Examples of orthopedic implants include, but are not limited to, a wide variety of pins, rods, screws, anchors, and plates used to anchor fractured bones while the bones heal or fuse together. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, an "interbody," "interbody implant," "fusion cage," or "cage" refers to an implant configured, designed, engineered, or arranged to be positioned between two other structures, organs, bones, or tissues within a patient. Often, the term interbody is used to refer to implants for use between vertebrae of a patient. Other terms that may be used herein for an interbody include, but are not limited to "fusion cage," "cage," "fusion device,", "spinal intervertebral device," "spinal interbody," or the like. In certain embodiments, an interbody may include an opening between a top side or surface of the interbody and a bottom side or surface of the interbody which may be used to hold graft material such as bone graft used in a fusion or fixation procedure.

As used herein, a "mesh" refers to a two or three dimensional structure having a plurality of openings or pores distributed within a longitudinal plane of the structure. A mesh may comprise a polygon mesh or a volumetric mesh. In 3D computer graphics and solid modeling, a polygon mesh is a collection of vertices, edges and faces that defines the shape of a polyhedral object. The faces usually consist of triangles (triangle mesh), quadrilaterals (quads), or other simple convex polygons (n-gons), since this simplifies rendering, but may also be more generally composed of concave polygons, or even polygons with holes. Volumetric meshes are distinct from polygon meshes in that they explicitly represent both the surface and volume of a structure, while polygon meshes only explicitly represent the surface (the volume is implicit). Volumetric meshes are a polygonal representation of the interior volume of an object. Unlike polygon meshes, which represent only the surface as polygons, volumetric meshes also discretize the interior structure of the object. (Search "Polygon Mesh" and "Volume mesh" on Wikipedia.com Jun. 5, 2021, Sep. 30, 2021. Accessed Aug. 30, 2021.)

Each of the plurality of openings or pores of a mesh may be of a common shape or a random shape. Alternatively, or in addition, the plurality of openings of a mesh may include pores having two or more geometric shapes. In addition, each of the plurality of pores of the mesh may be of a common size or diameter or may be of random sizes or diameters. Alternatively, or in addition, the plurality of pores of a mesh may include pores having two or more different diameter sizes. In certain embodiments, a mesh can include a single interconnected structure that occupies either a two dimensional or three dimensional space. In certain embodiments, a mesh can include a single structure that includes a plurality of wavy and curved edges that make up the mesh.

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/ or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure.

As used herein, "feature" refers to a distinctive attribute or aspect of something. (Search "feature" on google.com. Oxford Languages, 2021. Web. 20 Apr. 2021.) A feature may include one or more modifiers that identify one or more particular functions, attributes, advantages, or operations and/or particular structures relating to the feature. Examples of such modifiers applied to a feature, include, but are not limited to, "attachment feature," "securing feature," "alignment feature," "adjustment feature," "guide feature," "protruding feature," "engagement feature," "disengagement feature," and the like.

"Transition feature" refers to a model, modifier, formula, algorithm, modification factor, set of modification instructions or the like that influences how an aspect, attribute, or characteristic is to change from a first state or context to a second state or context. For example, in one embodiment, a transition feature may be a modifier for a formula in which the modifier changes based on how far a mesh position is from an intersection of the transition feature and a sidewall of a structure or model.

As used herein, "model" refers to an informative representation of an object, body, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.)

As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like.

As used herein, "locus" refers to a place or area where something is situated or occurs. Locus can also refer to a center of activity, attention, or concentration and/or the set of all points whose location is determined by stated conditions. (search "locus" on Merriam-Webster.com. Merriam-Webster, 2021. Web. 30 Aug. 2021. Modified.) A locus may be defined using various techniques, formulae, algorithms, representations, and/or models. For example, a geometric point, a line, a plane, 2D shape, or 3D shape in a three-dimensional coordinate system may define a locus. Alternatively, or in addition, a mathematical formula and/or an algorithm may define the locus for a mesh. A locus serves as a reference for another characteristic, attribute, or feature.

As used herein, a "Triply Periodic Minimal Surface" (TPMS) refers to a minimal surface in $\mathbb{R}^3$ that is invariant under a rank-3 lattice of translations within differential geometry. (Search 'Triply periodic minimal surface' on Wikipedia.com Jul. 19, 2020. Modified. Accessed Aug. 26, 2021.) TPMS is also a type of surface that designers can use in Computer Aided Design (CAD) software to generate lattice structures. TPMS structures can be organized into certain families such as the gyroid family and the lidnoid family.

A "gyroid triply periodic minimal surface" refers to a type of TPMS surface. A gyroid is a type of infinitely connected surface that Alan Schoen discovered in 1970. A gyroid surface is a type of triply periodic minimal surface (TPMS) that can be generated using a mesh generating software tool or feature of a CAD/CAM/CAE tool. Advantageously, a gyroid surface has a high surface area. A gyroid triply periodic minimal surface may originate from a triply periodic minimal surface (TPMS) field.

"Frame" refers to a structure organized, configured, designed, arranged, or engineered to provide structural support to one or more other devices, structure, components, and/or elements. In general a frame is rigid and provides structural support to one or more other components coupled to, integrated with, interfacing with, or connected to the frame. A frame may be a unitary component or a frame may be made up of a plurality of components. "Frame member" refers to a component, subcomponent, or part of a frame.

As used herein, "corner" refers to a point or area where converging lines, edges, or sides meet. Corner can also refer to an angular part or space between meeting lines, edges, or borders near the vertex of an angle. (search "corner" on Merriam-Webster.com. Merriam-Webster, 2021. Web. 30 Aug. 2021. Modified.)

"Curved corner" refers to a corner in which converging lines, edges, or sides meet by way of an arc that connects converging lines, edges, or sides. In a two-dimensional shape, a curved corner may join the converging lines, edges, or sides by way of a single curve. In a three-dimensional shape, a curved corner may join the converging lines, edges, or sides by way of an interior line segment and an external line segment. Certain implementations of a three-dimensional curved corner may include a curved interior line segment and a curved external line segment. In other implementations, either the interior line segment may form a right angle or an acute angle, the external line segment may form a right angle or an acute angle, or both the interior line segment and the external line segment may form a right angle or an acute angle.

As used herein, a "column" or "pillar" refers to a structure, device, component, member, system, assembly, or module structured, organized, configured, designed, arranged, or engineered to transmit, through compression, the weight and/or load of a structure above to other structural elements below the pillar or column. (Search 'Column' on Wikipedia.com Aug. 20, 2021. Modified. Accessed Aug. 30, 2021.) Generally, a column or pillar in a structure has a cylindrical shape.

"Cross section" or "cross-section" refers to the non-empty intersection of a body in three-dimensional space with a plane, or the analog in higher-dimensional spaces. (Search "cross section" on Wikipedia.com Mar. 7, 2022. Modified. Accessed Sep. 21, 2022.)

"Midpoint" refers to a point along a structure, object, component, plane, or line that is midway between opposite ends of the structure, object, component, plane, or line.

"Engagement feature" or "Engagement member" refers to an apparatus, instrument, structure, device, component, member, system, assembly or module structured, organized, configured, designed, arranged, or engineered to connect, join, link, couple to, or engage with another object, apparatus, instrument, structure, device, component, member, system, assembly or module either permanently or temporarily. The connection, coupling, linkage, or engagement may be a mechanical connection or interconnection.

As used herein, "mesh position" refers to a position of a point or area or space within a mesh as indicated by a three-dimensional coordinate system. In certain embodiments, a mesh position can be represented by a three-dimensional unit that is the smallest unit used in the generation, calculation, design, engineering, fabrication, rendering or formation of a mesh. This three dimensional unit may have an x, y, z coordinate in a three-dimensional coordinate system which may, or may not, be centered within the three-dimensional unit such a three-dimensional unit may be referred to herein as a mesh unit.

Alternatively, or in addition, a mesh position can be represented by a point having an x, y, z coordinate in a three-dimensional coordinate system which may, or may not, be a point of reference for the generation, calculation, design, engineering, fabrication, rendering or formation of a mesh.

"Mesh surface" refers to a surface formed by a mesh or lattice structure.

"Profile" refers to the outermost shape, view, or edge of an object. (Search "profile" on wordhippo.com. WordHippo, 2022. Web. Accessed 21 Sep. 2022). "Sidewall" refers to a wall forming a side of a structure, object, component, or system. (Search "sidewall" on wordhippo.com. WordHippo, 2022. Web. Accessed 21 Sep. 2022).

As used herein, "edge" refers to a structure or line where an object or area begins or ends. An edge can also refer to a narrow part adjacent to a border (search "edge" on Merriam-Webster.com. Merriam-Webster, 2021. Web. 3 Aug. 2021. Modified.) As used herein, "intersection" refers to a point, plane, line, or area where two or more other points, lines, planes, or areas each occupy the same space. As used herein, "origin" refers to a point of intersection of coordinate axes and/or a point at which something begins or rises or from which that thing derives (search "edge" on Merriam-Webster.com. Merriam-Webster, 2021. Web. 30 Aug. 2021. Modified.)

"Window" refers to an opening in a wall, door, roof, vehicle, system, component, or other structure that allows the passage of electromagnetic radiation including radio ways, x-rays, visible light, and the like. A window may also permit passage of sound, gases, fluids, liquids, or other elements. (Search "window" on Wikipedia.com Aug. 31, 2022. Modified. Accessed Sep. 21, 2022.). A window can be opaque, semi-opaque, translucent, or transparent.

"Radiolucent window" refers to a window that permits the passage of radiant energy and electromagnetic radiant energy, in particular, such as x-rays used in an x-ray machine and/or in a fluoroscopy imaging device.

"Stiffness" refers to the extent to which an object, structure, device, component, member, system, or assembly resists deformation in response to an applied force. It should be noted that the elastic modulus of a material is not the same as the stiffness of a component made from that material. Elastic modulus is a property of the constituent material; stiffness is a property of a structure or component of a structure, and hence stiffness is dependent upon various physical dimensions that describe that component. That is, the modulus is an intensive property of the material; stiffness, on the other hand, is an extensive property of the solid body, object, structure, device, component, member, system, or assembly that is dependent on the material and its shape and boundary conditions. (Search "stiffness" on Wikipedia-.com May 11, 2022. CC-BY-SA 3.0 Accessed Jul. 26, 2022. Modified.)

"Load" refers to a force, deformation, or acceleration applied to structure, component, apparatus, system, structural element, or the like. A load can cause stress, deformation, and displacement in a structure. (Search "structural load" on Wikipedia.com Sep. 1, 2022. Modified. Accessed Sep. 21, 2022.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

"Pore configuration relationship" refers to a relationship, or association, between an attribute, feature, or configuration aspect of a pore relative to one or more references and a determinable attribute. In certain embodiments, a pore configuration relationship includes a pore diameter (aka pore size) which is the attribute, a locus can serve as the reference, and a distance or range of distances between the pore and the reference is the determinable attribute.

"Position" refers to a place or location. (Search "position" on wordhippo.com. WordHippo, 2022. Web. Modified. Accessed 9 Aug. 2022.) "Relationship" refers to the way in which two or more concepts, structures, attributes, objects, or people are connected, related, influence each other, or are associated, or the state of being connected. (Search "relationship" on google.com. Oxford Languages, 2022. Modified Web. 23 Jun. 2022.)

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. An interbody implant for fusion of vertebrae of a patient, the interbody implant comprising:
   an anterior side, a posterior side, a cephalad side, a caudal side, a right side, and a left side;
   a proximal end and a distal end;
   a graft opening configured so that the anterior side, the posterior side, the right side, and the left side circumscribe the graft opening;
   a plurality of pillars configured to provide structural support;
   a mesh comprising a first set of pores having a first diameter based on a first relationship to a first locus and a second set of pores having a second diameter based on a second relationship to the first locus; and
   wherein:

31 at least one of the anterior side, posterior side, left side, right side, cephalad side, and caudal side comprise the mesh;

the plurality of pillars are connected by the mesh; and each of the plurality of pillars is positioned within the interbody implant so that the mesh extends between each of the plurality of pillars and the anterior side, the posterior side, the right side, the left side, and the graft opening.

2. The interbody implant of claim 1, wherein the mesh comprises a mesh surface formed within a gyroid triply periodic minimal surface (TPMS) field, the mesh surface volumized and wherein the mesh comprises pores that vary in diameter based on a position of a pore in relation to the first locus between a maximum pore size and a minimum pore size.

3. The interbody implant of claim 1, further comprising a third set of pores having diameters that vary between the first diameter and the second diameter.

4. The interbody implant of claim 1, wherein the mesh forms at least one of the anterior side, the posterior side, the left side, and the right side and the first locus intersects the mesh.

5. The interbody implant of claim 1, wherein the first relationship and the second relationship each comprise a distance of a set of pores from the first locus and wherein the mesh forms the posterior side and one of the left side and the right side and the first locus intersects the posterior side and the one of the left side and the right side.

6. The interbody implant of claim 1, wherein the first locus intersects the posterior side and the left side at a posterior side midpoint and at a left side midpoint.

7. The interbody implant of claim 1, wherein:

the first locus comprises an X shape; and wherein the first locus intersects a posterior side midpoint, an anterior side midpoint, a left side midpoint, and a right side midpoint.

8. The interbody implant of claim 1, wherein the mesh comprises a second locus and the pores of the mesh vary in diameter based on a position of a pore in relation to the first locus and the second locus.

9. The interbody implant of claim 1, wherein:

the posterior side is connected to the left side at a first corner, the left side is connected to the anterior side at a second corner, the anterior side is connected to the right side at a third corner, and the right side is connected to the posterior side at a fourth corner such that posterior side, left side, anterior side, and right side form an implant profile in a caudal view;

the plurality of pillars comprises four pillars;

each of the plurality of pillars is positioned in one of the first corner, the second corner, the third corner, and the fourth corner of the interbody implant;

the plurality of pillars cooperate to define a cross-section that forms a pillars profile smaller than the implant profile;

the graft opening that extends through the interbody implant from the cephalad side to the caudal side; and one or more of the plurality of pillars is positioned between two of the anterior side, left side, right side, and posterior side.

* * * * *